US010370416B2

(12) United States Patent
Zeng et al.

(10) Patent No.: US 10,370,416 B2
(45) Date of Patent: Aug. 6, 2019

(54) DUAL PURPOSE UNIVERSAL INFLUENZA VACCINE CONFERS PROTECTIVE IMMUNITY AGAINST ANTHRAX

(71) Applicant: Texas Tech University System, Lubbock, TX (US)

(72) Inventors: Mingtao Zeng, El Paso, TX (US); Maria T. Arevalo, Athens, GA (US); Junwei Li, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 105 days.

(21) Appl. No.: 15/446,315

(22) Filed: Mar. 1, 2017

(65) Prior Publication Data

US 2017/0253636 A1    Sep. 7, 2017

Related U.S. Application Data

(60) Provisional application No. 62/301,700, filed on Mar. 1, 2016.

(51) Int. Cl.
| | |
|---|---|
| *C07K 14/005* | (2006.01) |
| *G01N 33/50* | (2006.01) |
| *A61K 39/07* | (2006.01) |
| *A61K 39/12* | (2006.01) |
| *A61K 39/00* | (2006.01) |

(52) U.S. Cl.
CPC ............ *C07K 14/005* (2013.01); *A61K 39/07* (2013.01); *A61K 39/12* (2013.01); *G01N 33/5023* (2013.01); *G01N 33/5088* (2013.01); *A61K 2039/543* (2013.01); *A61K 2039/572* (2013.01); *A61K 2039/575* (2013.01); *A61K 2039/70* (2013.01); *C07K 2319/40* (2013.01); *C07K 2319/55* (2013.01); *C12N 2760/16122* (2013.01); *C12N 2760/16134* (2013.01); *C12N 2760/16143* (2013.01); *C12N 2760/16162* (2013.01); *G01N 2333/11* (2013.01); *G01N 2333/32* (2013.01)

(58) Field of Classification Search
None
See application file for complete search history.

(56) References Cited

U.S. PATENT DOCUMENTS 7,914,797 B2    3/2011    Arnon et al.
7,993,652 B2    8/2011    Neirynck et al.

FOREIGN PATENT DOCUMENTS

WO    WO2012/106231    *  8/2012

OTHER PUBLICATIONS

De Filette et al. Virology 2005, vol. 337, pp. 149-161.*
Shaw et al., Infection and Immunity May 2008, 76 (6) 2603-2611.*
George-Chandy et al., Infection and Immunity 2001, vol. 69, p. 5716, abstract only.*
Barbey-Martin, C., "An antibody that prevents the hemagglutinin low pH fusogenic transition." Virology, 2002, vol. 294, pp. 70-74.
Bedoya, F., et al., "Viral antigen induces differentiation of Foxp3+ natural regulatory T cells in influenza virus-infected mice." J Immunol., 2013, vol. 190, pp. 6115-6125.
Betts, R. J., et al., "Influenza A virus infection results in a robust, antigen-responsive, and widely disseminated Foxp3+ regulatory T cell response." J Virol., 2012, vol. 86, pp. 2817-2825.
Bommakanti, G., et al., "Design of an HA2-based *Escherichia coli* expressed influenza immunogen that protects mice from pathogenic challenge." Proc Natl Acad Sci USA., 2010, vol. 107, pp. 13701-13706.
Brincks, E. L., et al., "Antigen-specific memory regulatory CD4+ Foxp3+ T cells control memory responses to influenza virus infection." J Immunol., 2013, vol. 190, pp. 3438-3446.
Bui, H. H., et al., "Ab and T cell epitopes of influenza A virus, knowledge and opportunities." Proc Natl Acad Sci USA, 2007, vol. 104, pp. 246-251.
Comer, J. E., et al., "Direct inhibition of T-lymphocyte activation by anthrax toxins in vivo." Infect Immun., 2005, vol. 73, pp. 8275-8281.
Denkers, E. Y., et al., "Influence of antibody isotype on passive serotherapy of lymphoma." J Immunol., 1985, vol. 135, pp. 2183-2186.
Dreyfus, C., et al., "Highly conserved protective epitopes on influenza B viruses." Science (New York, N.Y.) 2012, vol. 337, pp. 1343-1348.
Duverger, A., et al., "Contributions of edema factor and protective antigen to the induction of protective immunity by Bacillus anthracis edema toxin as an intranasal adjuvant." J Immunol., 2010, vol. 185, pp. 5943-5952.
EBS. "BioThrax (R) Anthrax Vaccine Adsorbed Dosage and Administration." 2015, pp. 1-24.
Edwards, M. J., et al., "Two influenza A virus-specific Fabs neutralize by inhibiting virus attachment to target cells, while neutralization by their IgGs is complex and occurs simultaneously through fusion inhibition and attachment inhibition." Virology, 2000, vol. 278, pp. 423-435.
Gocnik, M., et al., "Antibodies induced by the HA2 glycopolypeptide of influenza virus hemagglutinin improve recovery from influenza A virus infection." J Gen Virol, 2008, vol. 89, pp. 958-967.
Hashemi, H., S. et al., "Immunization with M2e-displaying T7 bacteriophage nanoparticles protects against influenza A virus challenge." PLoS One, 2012, vol. 7: e45765.
Holsinger, L. J., et al., "Influenza virus M2 integral membrane protein is a homotetramer stabilized by formation of disulfide bonds." Virology, 1991, vol. 183, pp. 32-43.

(Continued)

*Primary Examiner* — Shanon A. Foley
*Assistant Examiner* — Myron G Hill
(74) *Attorney, Agent, or Firm* — Edwin S. Flores; Daniel J. Chalker; Chalker Flores, LLP

(57) ABSTRACT

The present invention includes antigenic fusion proteins, nucleic acids encoding the fusion proteins and methods of making and using the same, wherein the fusion protein comprises three or more different influenza A ectodomains of Matrix Protein 2 (M2e); one or more stem regions of an influenza A hemagglutinin 2 (HA2) protein; and optionally an anthrax antigen, wherein the fusion protein is immunogenic across strains.

37 Claims, 13 Drawing Sheets

Specification includes a Sequence Listing.

(56) References Cited

OTHER PUBLICATIONS

Hori, S., T. et al., "Control of regulatory T cell development by the transcription factor Foxp3." Science, 2003, vol. 299, pp. 1057-1061.

Jegerlehner, A., et al., "Influenza A vaccine based on the extracellular domain of M2: weak protection mediated via antibody-dependent NK cell activity." Journal of immunology, 2004, vol. 172, pp. 5598-5605.

Kang, S. M., et al., "Novel vaccines against influenza viruses." Virus research, 2011, vol. 162, pp. 31-38.

Kim, M. C., et al., "Microneedle patch delivery to the skin of virus-like particles containing heterologous M2e extracellular domains of influenza virus induces broad heterosubtypic cross-protection." J Control Release, 2015, vol. 210, pp. 208-216.

Kim, M. C., et al., "Multiple heterologous M2 extracellular domains presented on virus-like particles confer broader and stronger M2 immunity than live influenza A virus infection." Antiviral research, 2013, vol. 99, pp. 328-335.

Kim, M. C., et al., "Supplementation of influenza split vaccines with conserved M2 ectodomains overcomes strain specificity and provides long-term cross protection." Molecular therapy: the journal of the American Society of Gene Therapy, 2014, vol. 22, pp. 1364-1374.

Kim, M. C., et al., "Virus-like particles containing multiple M2 extracellular domains confer improved cross-protection against various subtypes of influenza virus." Mol Ther., 2013, vol. 21, pp. 485-492.

Kolla, R. V., et al., "Complement C3d conjugation to anthrax protective antigen promotes a rapid, sustained, and protective antibody response." PLoS One, 2007, vol. 2, pp. e1044.

Li, J., et al., "Intranasal immunization with influenza antigens conjugated with cholera toxin subunit B stimulates broad spectrum immunity against influenza viruses." Human vaccines & immunotherapeutics, 2014, vol. 10, No. 5, pp. 1211-1220.

McEvers, K., et al., "Modified anthrax fusion proteins deliver HIV antigens through MHC Class I and II pathways." Vaccine, 2005, vol. 23, pp. 4128-4135.

Moise L., et al. "Smarter vaccine design will circumvent regulatory T cell-mediated evasion in chronic HIV and HCV infection." Frontiers in microbiology, 2014, vol. 5, pp. 502.

Pica, N., et al., "Toward a universal influenza virus vaccine: prospects and challenges." Annual review of medicine, 2013, vol. 64, pp. 189-202.

Pinto, L. H., er al., "Controlling influenza virus replication by inhibiting its proton channel." Molecular bioSystems, 2007, vol. 3, pp. 18-23.

Quesnel-Hellmann, A., et al., "Evidence for adjuvanticity of anthrax edema toxin." Vaccine, 2006, vol. 24, pp. 699-702.

Reperant, L. A., et al., "Avian influenza viruses in mammals." Revue scientifique et technique (International Office of Epizootics) 2009, vol. 28, pp. 137-159.

Roose, K., et al., "Pandemic preparedness: toward a universal influenza vaccine." Drug news & perspectives, 2009, vol. 22, pp. 80-92.

Shaw, C. A., et al., "Both CD4+ and CD8+ T cells respond to antigens fused to anthrax lethal toxin." Infect Immun., 2008, vol. 76, pp. 2603-2611.

Song, J. M., et al., "Influenza virus-like particles containing M2 induce broadly cross protective immunity." PLoS One, 2011, vol. 6, pp. e14538.

Twentyman, P. R., et al., "A study of some variables in a tetrazolium dye (MTT) based assay for cell growth and chemosensitivity." Br J Cancer., 1987, vol. 56, pp. 279-285.

Wang, B. Z., et al., "Enhanced influenza virus-like particle vaccines containing the extracellular domain of matrix protein 2 and a Toll-like receptor ligand." Clin Vaccine Immunol., 2012, vol. 19, pp. 1119-1125.

Wang, T. T., et al., "Vaccination with a synthetic peptide from the influenza virus hemagglutinin provides protection against distinct viral subtypes." Proc Natl Acad Sci USA., 2010, vol. 107, pp. 18979-18984.

Xu, Q., et al., "Detoxified lethal toxin as a potential mucosal vaccine against anthrax." Clin Vaccine Immunol., 2008, vol. 15, pp. 612-616.

Xu, Q., et al., "Transcriptional stimulation of anthrax toxin receptors by anthrax edema toxin and Bacillus anthracis Sterne spore." Microb Pathog., 2007, vol. 43, pp. 37-45. PMID: 17459655.

Zeng, M., et al., "N-fragment of edema factor as a candidate antigen for immunization against anthrax." Vaccine, 2006, vol. 24, pp. 662-670.

Zeng, M., et al., "Protection against anthrax by needle-free mucosal immunization with human anthrax vaccine." Vaccine, 2007, vol. 25, pp. 3588-3594.

* cited by examiner

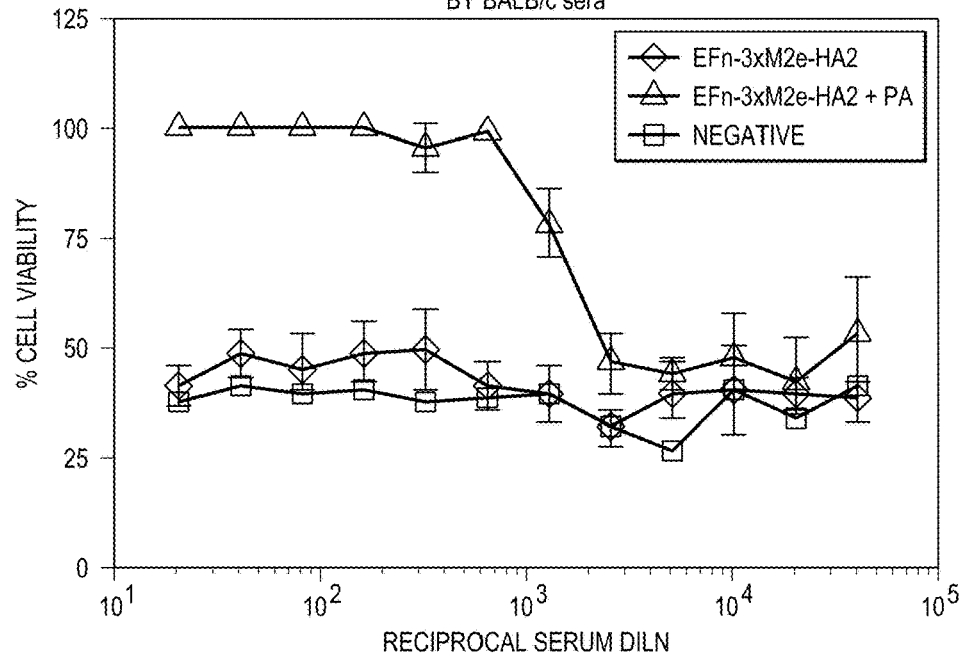
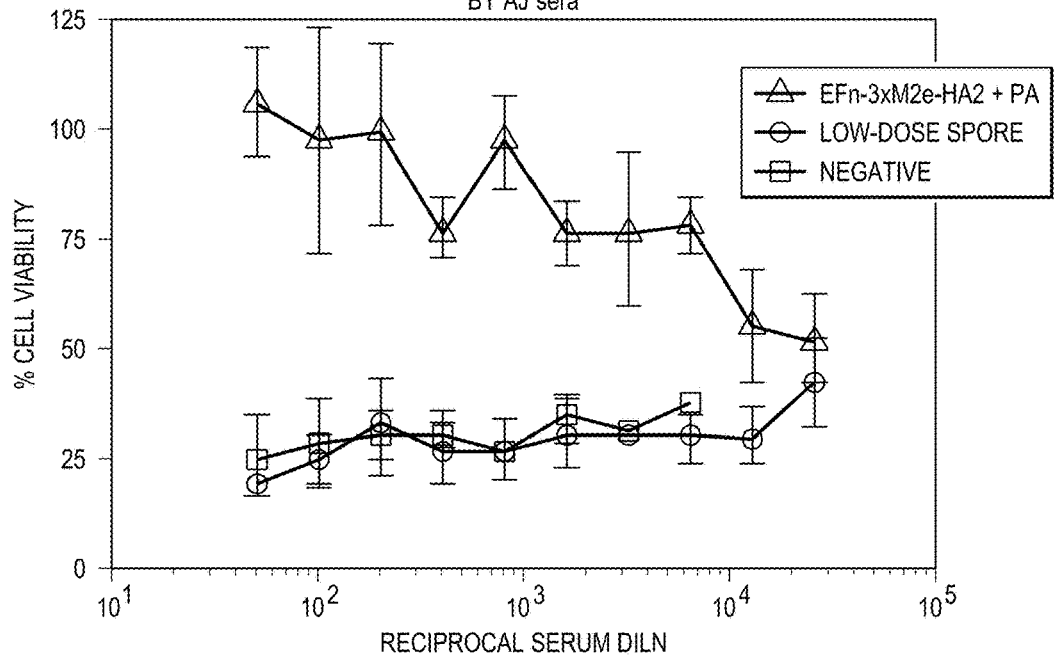

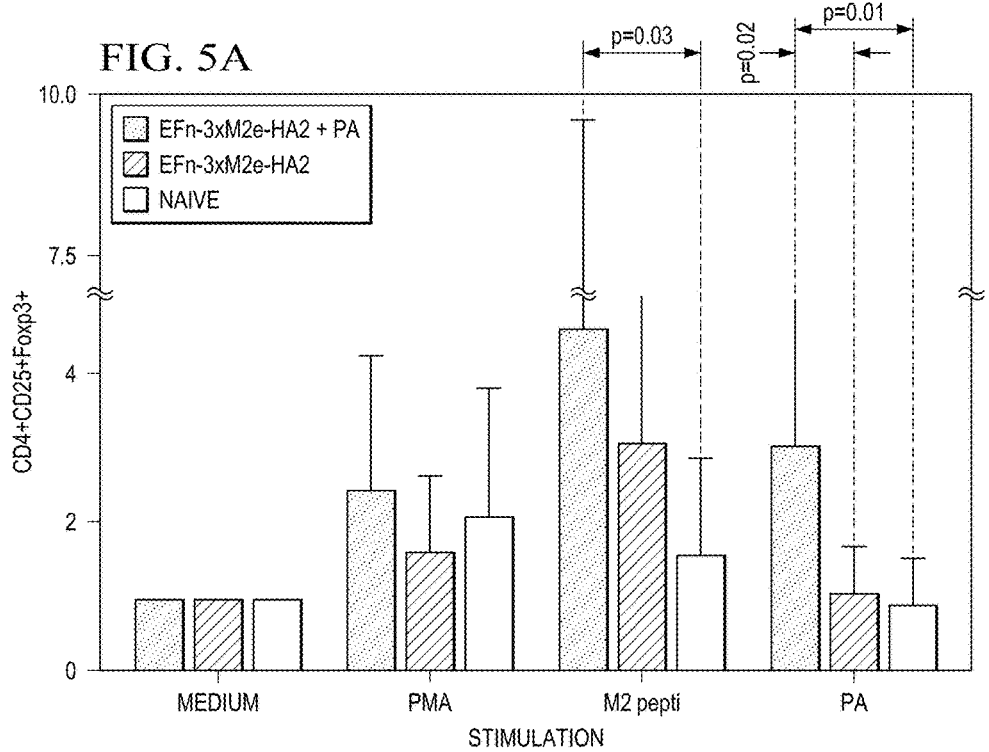

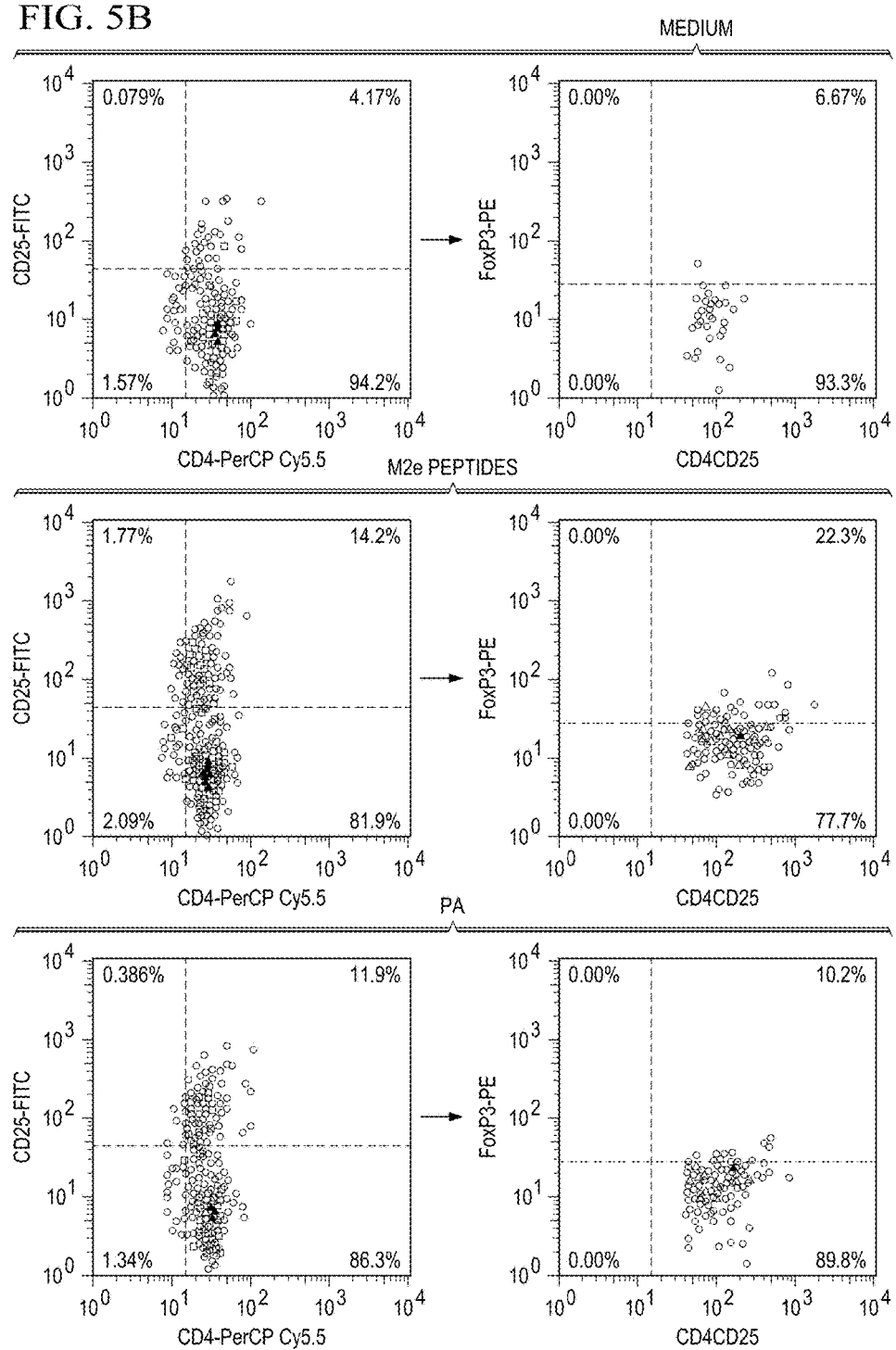

FIG. 6B

DUAL PURPOSE UNIVERSAL INFLUENZA VACCINE CONFERS PROTECTIVE IMMUNITY AGAINST ANTHRAX

CROSS-REFERENCE TO RELATED APPLICATIONS

This application claims priority to U.S. Provisional Application Ser. No. 62/301,700, filed Mar. 1, 2016, the entire contents of which are incorporated herein by reference.

STATEMENT OF FEDERALLY FUNDED RESEARCH

This invention was made with U.S. Government support by the NIH/NIAID grant number R01 AI072139. The government has certain rights in this invention.

TECHNICAL FIELD OF THE INVENTION

The present invention relates in general to the field of vaccines, and more particularly, to an universal influenza vaccine confers protective immunity against anthrax.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Mar. 1, 2017, is named TECH1145_SeqList.txt and is 10 kilobytes in size.

BACKGROUND OF THE INVENTION

Without limiting the scope of the invention, its background is described in connection with influenza vaccines.

Influenza viral illness, like many other microbial diseases can be prevented through vaccination. However, vaccine development against infectious diseases such as influenza is often a challenge because multiple serotypes, subtypes, and strains exist. Furthermore, new strains, including potentially pandemic strains are continuously emerging. Thus, simple monovalent vaccine formulations for these pathogens and their derivatives are not sufficient for long-term control. Development of multivalent formulations for broad-range reactivity and protection is crucial.

In one example, U.S. Pat. No. 7,993,652, issued to Neirynck, et al., is directed to immunoprotective influenza antigen and its use in vaccination. Briefly, these inventors teach an influenza antigen that includes a fusion product with at least the extracellular part of a conserved influenza membrane protein or a functional fragment thereof and a presenting carrier, which may be a presenting (poly)peptide or a non-peptidic structure, such as glycans, peptide mimetics, or synthetic polymers. The invention is said to be a vaccine against influenza that includes at least an antigen of the invention, optionally in the presence of one or more excipients. Finally, the invention is also said to include the use of the antigen in a method for preparing the antigen and acceptor cells expressing the antigen.

U.S. Pat. No. 7,914,797, issued to Arnon, et al., and is directed to an influenza vaccine, specifically, influenza vaccines for human and veterinary use. More particularly, the invention is said to provide a vaccine capable of long term and cross-strain protection by including at least two influenza virus epitopes expressed as a chimeric polypeptide wherein at least one epitope is influenza A virus matrix protein epitope and the second epitope is a hemagglutinin peptide epitope.

SUMMARY OF THE INVENTION

In one embodiment, the present invention includes an antigenic fusion protein comprising: three or more different influenza A ectodomains of matrix protein 2 (M2e); one or more stem regions of an influenza A hemagglutinin 2 (HA2) protein; and an anthrax antigen, wherein the fusion protein is immunogenic across strains. In one aspect, the fusion protein further comprises, or is provided with, an adjuvant selected from at least one of anthrax protective antigen (PA), cholera toxin B subunit, flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles. In another aspect, the two or more different influenza ectodomains are selected from H1N1, H3N2, or H5N1. In another aspect, the fusion protein further comprises the stem region of the influenza A hemagglutinin 2 (HA2) protein from different influenza virus A strains. In another aspect, the antigen is formulated into a vaccine. In another aspect, the antigen is formulated into a vaccine further adapted for intraperitoneal, subcutaneous, intranasal, intramuscular, oral, topical or transdermal administration. In another aspect, the antigen further comprises at least one of a pharmaceutically acceptable diluent, excipient, carrier, solubilizing agent, emulsifying agent, or preservative. In another aspect, the antigen comprises 3, 4, 5, 6, 7, 8, 9, or 10 ectodomains of influenza A Matrix Protein 2 (M2e). In another aspect, the antigen comprises 3, 4, 5, 6, 7, 8, 9, or 10 stem region of an influenza A hemagglutinin 2 (HA2) protein. In another aspect, the antigen comprises 3 ectodomains of influenza A Matrix Protein 2 (M2e) separated by peptide linkers comprising one to 20 amino acids. In another aspect, the antigen is a fusion protein that comprises SEQ ID NOS.: 1, 2, 3, 4, 5 and 6. In another aspect, the antigen is a fusion protein that comprises, in the following order, SEQ ID NOS.: 1, 2, 3, 4, 5 and 6. In another aspect, the antigen is a fusion protein that comprises SEQ ID NOS.: 1, 2, 3, 4, 5 and 6 separated by one or more linkers. Another embodiment includes a nucleic acid encoding the fusion protein comprising: two or more different influenza A ectodomains of matrix protein 2 (M2e); one or more stem regions of an influenza A hemagglutinin 2 (HA2) protein; and an anthrax antigen, wherein the fusion protein is immunogenic across strains.

Another embodiment of the present invention includes a method of making a mucosal vaccine against influenza A comprising: combining two or more different influenza A ectodomains of matrix protein 2 (M2e); one or more stem regions of an influenza A hemagglutinin 2 (HA2) protein; and an anthrax antigen into an antigen that is immunogenic across strains. In one aspect, the fusion protein further comprises, or is provided with, an adjuvant selected from at least one of anthrax protective antigen (PA), cholera toxin B subunit, flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles. In another aspect, the two or more different influenza ectodomains are selected from H1N1, H3N2, or H5N1. In another aspect, the method further comprises obtaining the stem region of the influenza A hemagglutinin 2 (HA2) protein from different influenza virus A strains. In another aspect, the antigen is formulated into a vaccine. In another aspect, the antigen is formulated into a vaccine further adapted for intraperitoneal, subcutaneous, intranasal, intramuscular, oral, topical or transdermal administration. In another aspect, the antigen further comprises at least one of a pharmaceutically acceptable diluent, excipient, carrier, solubilizing agent, emulsifying agent, or preservative. In another aspect, the antigen comprises 3, 4, 5, 6, 7, 8, 9 or 10 ectodomains of influenza A Matrix Protein 2 (M2e). In another aspect, the antigen comprises 3, 4, 5, 6, 7, 8, 9 or 10 stem region of an influenza A hemagglutinin 2 (HA2) protein. In another aspect, the antigen comprises 3 ectodomains of influenza A Matrix Protein 2 (M2e) separated by peptide linkers comprising one to 20 amino acids. In another aspect, the antigen is a fusion protein that comprises SEQ ID NOS.: 1, 2, 3, 4, 5 and 6. In another aspect, the antigen is a fusion protein that comprises, in the following order, SEQ ID NOS.: 1, 2, 3, 4, 5 and 6. In another aspect, the antigen is a fusion protein that comprises SEQ ID NOS.: 1, 2, 3, 4, 5 and 6 separated by one or more linkers. In another aspect, the linkers have the sequences Ala-Ala-Ala or Gly-Ser. In another aspect, the antigen is a fusion protein that comprises three or more amino acids peptides of SEQ ID NOS.: 11, 12, and 13, at least one peptide of amino acid sequence SEQ ID NOS.: 9 or 10, and a peptide of SEQ ID NO.: 14. In another aspect, the fusion protein is, in order, SEQ ID NO.: 14, SEQ ID NOS.: 11, 12, and 13 in any order, and SEQ ID NOS.: 9 or 10. In another aspect, the fusion protein is, in order, SEQ ID NOS.: 11, 12, and 13 in any order, and SEQ ID NOS.: 9 or 10.

Yet another embodiments includes a method evaluating a candidate drug believed to provide cross-immunity against influenza A and anthrax, the method comprising: (a) measuring the immune response from a set of patients suspected of having or being exposed to influenza A; (b) administering a candidate drug to a first subset of the patients, and a placebo to a second subset of the patients, wherein the candidate drug comprises: two or more different influenza A ectodomains of matrix protein 2 (M2e); one or more stem regions of an influenza A hemagglutinin 2 (HA2) protein; and an anthrax antigen into a fusion protein that is immunogenic across strains; (c) repeating step (a) after the administration of the candidate drug or the placebo; and (d) determining if the candidate drug triggers an increase in the immune response against two or more influenza A strains and anthrax that is statistically significant as compared to any increase occurring in the second subset of patients, wherein a statistically significant increase indicates that the candidate drug is useful in treating two or more strains of influenza A and anthrax. In another aspect, the linkers have the sequences Ala-Ala-Ala or Gly-Ser. In another aspect, the antigen is a fusion protein that comprises three or more amino acids peptides of SEQ ID NOS.: 11, 12, and 13, at least one peptide of amino acid sequence SEQ ID NOS.: 9 or 10, and a peptide of SEQ ID NO.: 14. In another aspect, the fusion protein is, in order, SEQ ID NO.: 14, SEQ ID NOS.: 11, 12, and 13 in any order, and SEQ ID NOS.: 9 or 10. In another aspect, the fusion protein is, in order, SEQ ID NOS.: 11, 12, and 13 in any order, and SEQ ID NOS.: 9 or 10.

Yet another embodiment of the present invention includes an isolated immune response stimulating fusion protein against influenza A comprising: two or more different influenza A ectodomains of matrix protein 2 (M2e); one or more stem regions of an influenza A hemagglutinin 2 (HA2) protein comprising SEQ ID NOS.: 1, 2, 3, 4 and 5; and optionally an anthrax antigen into a fusion protein that is immunogenic across strains. In another aspect, the linkers have the sequences Ala-Ala-Ala or Gly-Ser. In another aspect, the antigen is a fusion protein that comprises three or more amino acids peptides of SEQ ID NOS.: 11, 12, and 13, at least one peptide of amino acid sequence SEQ ID NOS 9 or 10, and a peptide of SEQ ID NO.: 14. In another aspect, the fusion protein is, in order, SEQ ID NO.: 14, SEQ ID NOS.: 11, 12, and 13 in any order, and SEQ ID NOS.: 9 or 10. In another aspect, the fusion protein is, in order, SEQ ID NOS.: 11, 12, and 13 in any order, and SEQ ID NOS.: 9 or 10.

BRIEF DESCRIPTION OF THE DRAWINGS

For a more complete understanding of the features and advantages of the present invention, reference is now made to the detailed description of the invention along with the accompanying figures and in which:

FIG. 1A is a schematic representation of vaccine constructs: M2, EFn-M2, and EFn-3×M2e-HA2. FIG. 1B shows representative verifications by Western Blot of recombinant proteins M2, EFn-M2, and EFn-3×M2e-HA2 are shown. F—purification flowthrough, W—wash, and E—elution.

FIGS. 2A to 2C show vaccine construct-induced serum reactivity to recombinant influenza H5N1 M2 and 3×M2e-HA2 antigens. FIG. 2A shows antibody responses against recombinant H5N1 M2 protein produced in E. coli were measured using ELISA for BALB/c mice intranasally vaccinated as follows: EFn-M2, 3 dose; EFn-M2+PA, 3 doses; EFn-3×M2e-HA2, 3 doses; EFn-3×M2e-HA2+PA, 3 doses; M2, 3 doses; low-dose PR8 virus, 1 dose; and no immunization or negative control. FIG. 2B shows sera from the same groups were evaluated for reactivity to 3×M2e-HA2. The results are expressed as the mean+SEM for each group. FIG. 2C shows pooled sera that was evaluated for reactivity to peptides from A/California/7/09 (H1N1) or H7N9 A/Anhui/1/2013 (H7N9), or recombinant, full-length HA protein from A/Vietnam/1203/2004 (H5N1).

FIGS. 3A to 3C show the survival of vaccinated mice following lethal challenge with influenza virus. Immunized and naïve (negative control) mice were challenged with PR8 (H1N1) 2×10⁵ PFU. FIG. 3A shows EFn-M2 (N=14), EFn-M2+PA (N=16), EFn-3×M2e-HA (N=16), EFn-3×M2e-HA2+PA, (N=14) and naïve mice (N=16). For mice immunized with M2 or PR8, N=11. Kaplan-Meier Survival curve of vaccinated mice that represent the results of two separate studies. FIG. 3B shows mice were immunized with EFn-3×M2e-HA2+PA as before, or a low-dose of CA09 virus. Naïve and immunized groups (N=8 per group) were then challenged with 1×10⁵ PFU CA09 virus. Kaplan-Meier Survival analysis is shown. FIG. 3C shows unvaccinated mice received 200 μl of pooled sera from naïve mice or from mice immunized with a low-dose of PR8, EFn-3×M2e-HA2, or EFn-3×M2e-HA2+PA at 24 h prior to lethal challenge with PR8 virus (N=8 per group).

FIGS. 4A to 4F demonstrate immunity against anthrax. Sera was diluted and incubated with LeTx preparations prior to addition to Raw 264.7 cells. An MTT viability assay was performed 7 h later, and results were normalized to viable cells (no LeTx added). FIG. 4A shows the neutralization responses by sera from immunized (FIG. 4A) BALB/c mice (LF 320 ng/ml+PA 480 ng/ml) and (FIG. 4B) A/J mice (LF 1 µg/ml+1.5 µg/ml are shown). A/J mice were immunized with 50 *B. anthracis* Sterne strain spores once or with EFn-3×M2e-HA+PA thrice, as before. Recombinant *B. anthracis* proteins obtained from BEI Resources were then used to measure (FIG. 4C) serum total IgG to EF and (FIG. 4D) serum total IgG to PA; results are expressed as mean±SEM for each group with N=8 mice. FIG. 4E shows the results when these mice were then challenged with $5 \times 10^4$ *B. anthracis* Sterne spores. Kaplan-Meier Survival curves are shown. FIG. 4F shows EFn-3×M2e-HA2 dose response against lethal challenge with $1.8 \times 10^5$ spores.

FIGS. 5A and 5B show that Treg cells response to vaccine antigens. Splenic mononuclear cells were isolated from the spleens of mice and stimulated with various antigens. FIG. 5A shows the results of $1 \times 10^6$ cells were stimulated with (1) DMEM medium as no-stimulated control or 100 ng/ml of (2) PMA as positive control, 10 µg/ml of (3) M2e peptides derived from A/New York/348/03 H1N1, or (4) recombinant anthrax PA, or (5) recombinant EF for three days prior to ICS and FACS analyses. Results represent mean+SEM for N=15 mice (EFn-3×M2e-HA2+PA and Control) and N=13 mice (EFn-3×M2e-HA2). Two-way, two-tail ANOVA was performed and found that EFn-3×M2e-HA2+PA group compared with control group and EFn-3×M2e-HA2 group significantly differed by immunization ($p=0.0016$; $p=0.0206$, respectively). FIG. 5B is a FACS analysis of CD4+CD25+ Foxp3+ in spleen cells from EFn-3×M2e-HA2+PA vaccinated mice. The CD4+CD25+ cells were selected to analyze FoxP3+ population. Upper plots represent no-stimulation control; middle plots are stimulation with M2e peptides, and bottom plots are stimulation with recombinant PA.

FIGS. 6A and 6B show the verification of influenza M2e-specific T cell immunity by tetramer staining. Spleen mononuclear cells were isolated from naïve and immunized mice (N=4 mice per group). FIG. 6A shows CD3+/CD8+ lymphocytes that were analyzed for binding to H-2K(d)/M2e peptide (VETPIRNEW) tetramers labeled with APC. FIG. 6B shows CD3+/CD4+ lymphocytes analyzed for binding to I-A(d)/M2e peptide (SLLTEVETPIRNEWGS) tetramers labeled with PE.

DETAILED DESCRIPTION OF THE INVENTION

Figure 1A:
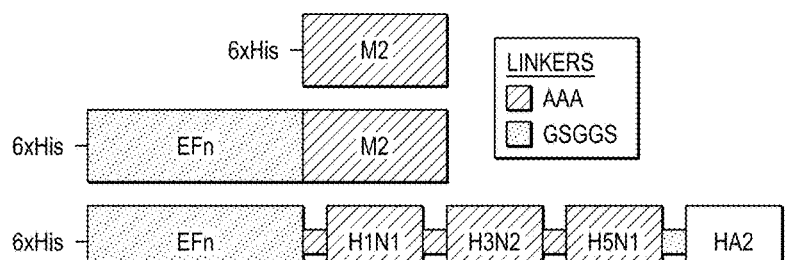
FIGS. 1A and 1B show the vaccine construct design and verification.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "antigen" refers to a molecule with one or more epitopes that stimulate a host's immune system to make a secretory, humoral and/or cellular antigen-specific response against two or more strains of influenza A in a vertebrate. The term is also used interchangeably with "immunogen." In one example, the present invention includes two specific antigens that can be a complete protein, portions of a protein, peptides, fusion proteins, glycosylated proteins and combinations thereof.

As used herein, the term "adjuvant" refers to a substance that enhances, specifically or non-specifically, an immune response to an antigen. Non-limiting examples of adjuvants for use with the present invention include cholera toxin B subunit, flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles.

As used herein, the term "fusion protein" refers to a single protein that includes a combination of more than one protein, e.g., a single protein that includes both an influenza A antigen from two or more different strains and an anthrax antigen.

As used herein, the term "gene" refers to a recombinant nucleic acid segment that expresses a protein, polypeptide or peptide. In one example, a recombinant gene is assembled that expresses a single protein that includes both an influenza A antigen from two or more different strains and an anthrax antigen. As will be understood by those in the art, this functional term includes genomic sequences, cDNA sequences, probes, oligonucleotides or fragments thereof (and combinations thereof), as well as gene products, including those that may have been designed and/or altered by the user. Purified genes, nucleic acids, protein and the like are used to refer to these entities when identified and separated from at least one contaminating nucleic acid or protein with which it is ordinarily associated.

As used herein, the terms "protein", "polypeptide" and "peptide" refer to compounds comprising amino acids joined via peptide bonds and are used interchangeably.

As used herein, the term "vector" is used in reference to nucleic acid molecules that transfer DNA segment(s) from one cell to another. The term "vehicle" is sometimes used interchangeably with "vector." The term "vector" as used herein also includes expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes or eukaryotes usually include a promoter, an operator (optional), and a ribosome binding site, often along with other sequences. Eukaryotic cells are known to use promoters, enhancers, and termination and polyadenylation signals. The term "vector" may be used to describe the use of a carrier or other delivery system or organism to deliver the antigen(s) of the present invention to a host in order to trigger an immune response as part of a vaccine. Non-limiting examples of these vaccine vectors include viruses, bacteria, protozoans, cells (e.g., homologous or heterologous), etc., which may be live, live-attenuated, heat-killed, mechanically-killed, chemically-killed, recombinant (e.g., peptides, proteins and the like), as will be known to those skilled in the art of vaccine preparation. The skilled artisan will readily recognize the type of "vector" to which this specification and claims refer based on the description of the materials and methods used and described herein.

Preventative influenza vaccines must be reformulated annually because of antigen shift and drift of circulating influenza viral strains. However, seasonal vaccines do not always match the circulating strains, and there is the ever-present threat that avian influenza viruses may adapt to humans. Hence, a universal influenza vaccine is needed to provide protective immunity against a broad range of influenza viruses. The inventors designed an influenza antigen consisting of 3 tandem M2e repeats plus HA2, in combination with a detoxified anthrax edema toxin delivery system (EFn plus PA) to enhance immune responses. The EFn-3×M2e-HA2 plus PA vaccine formulation elicited robust, antigen-specific, IgG responses; and was protective against heterologous influenza viral challenge when intranasally delivered to mice three times. Moreover, use of the detoxified anthrax toxin system as an adjuvant had the additional benefit of generating protective immunity against anthrax. Thus, this novel vaccine strategy addresses two major emerging public health and biodefense threats.

Influenza viral illness, like many other microbial diseases, can be prevented through vaccination. However, vaccine development against infectious diseases such as influenza is often a challenge because multiple isotypes and strains exist. Furthermore, new strains, including potentially pandemic strains, are continuously emerging. Thus, simple monovalent vaccine formulations for these pathogens and their derivatives are not sufficient for long-term control. Development of multivalent formulations for broad-range reactivity and protection is crucial.

Conserved epitopes, including regions of hemagglutinin (HA), nucleoprotein (NP), or matrix protein 2 (M2) of influenza virus can elicit heterosubtypic immunity (1-3). HA is the major surface antigen on influenza virus and is composed of HA1 and HA2 subunits. The HA1 region is highly variable among influenza A strains, while HA2 is more conserved. HA2-specific antibodies reduce the replication of influenza by inhibiting fusion (4) and providing protection in mice (5, 6). M2 of influenza A virus is a tetrameric ion channel protein that is targeted by antivirals amantadine and rimantadine (7). The N-terminal, 23-amino acid peptide of M2 (M2e) is highly conserved among all influenza A viruses (8). Antibodies against M2 reduce viral spread (9), and virus-like particles containing M2 or M2e elicit cross-strain reactive antibodies, specific T cell responses, and confer heterosubtypic protection in mice (10-14). Because influenza virus is a respiratory pathogen, intranasal delivery of these conserved, immunogenic antigens may be ideal.

For an effective, intranasal vaccine strategy, a compatible adjuvant system is important. Detoxified anthrax toxins can be used as adjuvants for vaccine development (15-19). An additional advantage to this approach is the induction of protective immunity against anthrax, another infectious biological agent with urgency for an improved vaccine strategy. Anthrax is a severe infectious disease caused by *Bacillus anthracis* which produces a tripartite exotoxin comprised of protective antigen (PA), lethal factor (LF), and edema factor (EF). PA in combination with EF forms edema toxin (EdTx) and PA in combination with LF forms lethal toxin (LeTx). Individually, PA, EF, and LF are non-toxic. PA mediates entry of EF and LF into the cytosol of susceptible cells by receptor-mediated endocytosis. The N-terminal region of EF (EFn) is critical for binding to PA and subsequent translocation into cytosol. EFn (1-120 residues) lacks cytotoxicity, but its antigenicity is preserved, and can potentially be used in the formulation of a mucosal vaccine against anthrax (20-23). Vaccination with the current licensed vaccine requires a lengthy and complicated schedule: 5 intramuscular injections (0 and 4 weeks, then 6, 12, and 18 months) followed by annual boosters (24). Thus, the current approach is inadequate in the case of a bioterrorist attack with anthrax.

In this study, a vaccine based on conserved influenza antigens was designed, in combination with an anthrax antigen delivery system. The ultimate goal is to create a dual vaccine that would provide broad cross-strain protection across various influenza virus subtypes, while also eliciting protective immunity against anthrax. Multiple vaccine formulations were evaluated in mice for their abilities to confer humoral, T cell, and protective immunities.

Vaccine candidate design, production, and purification. For 3×M2e-HA2 antigen design, the aligned HA2 of H1N1, H3N2, H5N1, H7N1, H7N3 and H9N2 amino acid gene sequences from the Influenza Virus Resource. The most common amino acids in each position were used to create an artificial, centralized, HA2 sequence. Next, a tandem of M2es from A/California/04/2009 (H1N1), A/Hong Kong/1/1968 (H3N2), and A/Vietnam/1204/2004 (H5N1) influenza viruses was created and linked with the centralized HA2. The anthrax EFn gene sequence (20) was added upstream of the 3×M2e-HA2. In addition, Ala-Ala-Ala or Gly-Ser linkers were designed in between individual gene segments. The artificial gene sequence was codon-optimized for *E. coli* and synthesized by GenScript, Inc. (Piscataway, N.J.). The full-length, avian influenza A (H5N1) M2 DNA sequence was synthesized by Retrogen, Inc. (San Diego, Calif.). M2, 3×M2e-HA2, and EFn-3×M2e-HA2 genes were inserted into prokaryotic plasmid pET200/D-TOPO (Life Technologies, Carlsbad, Calif.). For EFn-M2, the EFn sequence was cloned upstream of the full length M2 sequence in the pET200/D-TOPO plasmid. All expression plasmids were transformed in BL21 Star™ (DE3) competent cells (Life Technologies). Transformed cells were cultured in LB medium with 50 µg/ml of kanamycin to OD600 of 0.5, and expression was induced with 0.001-1 mM Isopropyl β-D-1-thiogalactopyranoside (IPTG) depending on the protein, and harvested 2-4 h later. The expressed proteins contained 6×His tags and were purified by affinity chromatography using Ni-NTA agarose beads. For M2, 3×M2e-HA2, and EFn-3×M2e-HA2, purifications were performed with denaturing buffer: 100 mM $NaH_2PO_4$, 10 mM Tris, and 8 M urea with varying imidazole concentrations of 10-250 mM (all pH=8). EFn-M2 was purified with native buffer: 10 mM Tris, 0.1 mM EDTA, and 500 mM NaCl with varying imidazole concentrations of 10-250 mM (all pH=8). Purified proteins were dialyzed and concentrated using ultracentrifugal filter devices (Millipore, Billerica, Mass.) with dialysis buffer: PBS with 10% glycerol. Proteins were stored at −80° C. prior to use for vaccination. Antigen sequences and vaccine candidate designs are shown in Table I and FIG. 1A, respectively. Proteins were verified by Western Blot (FIG. 1B) using anti-His-G-AP (Life Technologies), rabbit anti-Avian influenza M2 (Thermo Scientific, Lafayette, Colo.), or rabbit anti-EF (gift from Dr. Stephen Leppla).

TABLE I

Influenza-Anthrax Vaccine Antigens

| Antigen | Sequence |
|---|---|
| | Influenza |
| HA2 | GGTCTATTTGGAGCCATTGCCGGTTTTATTGAAGGGGGATGGACTGGAA |
| | TGATAGATGGATGGTATGGTTATCATCATCAGAATGAACAGGGATCAGG |
| | CTATGCAGCGGATCAAAAAAGCACACAAAATGCCATTGACGGGATTAC |
| | AAACAAGGTGAACTCTGTTATCGAGAAAATGAACACTCAATTCACAGCT |
| | GTGGGTAAAGAATTCAACAAATTAGAAAAAAGGATTGAAAATTTAAAT |
| | AAAAAAGTTGATGATGGATTTCTGGACATTTGGACATATAATGCAGAAT |
| | TGTTAGTTCTACTGGAAAATGAAAGGACTCTGGATTTCCATGACTCAAA |
| | TGTGAAGAATCTGTATGAGAAAGTAAAAAGCCAATTAAAGAATAATGC |
| | CAAAGAAATCGGAAATGGATGTTTTGAGTTCTACCACAAGTGTGACAAT |
| | GAATGCATGGAAAGTGTAAGAAATGGGACTTATGATTATCCC (SEQ ID NO. 1) |
| Avian M2 (H5N1) | ATGTCTCTGCTGACCGAAGTTGAAACCCCGACCCGTAACGAATGGGAAT |
| | GCCGTTGCTCTGACTCTTCTGACCCGATCGTTGTTGCGGCGAACATCATC |
| | GGTATCCTGCACCTGATCCTGTGGATCCTGGACCGTCTGTTCTTCAAATG |
| | CATCTACCGTCGTCTGAAGTACGGTCTGAAACGTGGTCCGGCGACCGCG |
| | GGTGTTCCAGAATCTATGCGTGAAGAATACCGTCAGGAACAGCAGTCTG |
| | CGGTTGACGTTGATGACGGTCACTTCGTTAACATCGAACTGGAATAA (SEQ ID NO. 2) |
| M2e (H1N1) | AGTCTTCTAACCGAGGTCGAAACGCCTACCAGAAGCGAATGGGAGTGC |
| | AGATGCAGCGATTCAAGTGAT (SEQ ID NO. 3) |
| M2e (H3N2) | AGCCTTCTAACCGAGGTCGAAACGCCTATCAGAAACGAATGGGGGTGC |
| | AGATGCAACGATTCAAGTGAC (SEQ ID NO. 4) |
| M2e (H5N1) | AGTCTTCTAACCGAGGTCGAAACGCCTACCAGAAACGAATGGGAGTGC |
| | AGATGCAGCGATTCAAGTGAT (SEQ ID NO. 5) |
| | Anthrax |
| EFn | ATGAATGAACATTACACTGAGAGTGATATTAAAAGAAACCATAAAACT |
| | GAAAAAAATAAAACTGAAAAAGAAAAATTTAAAGACAGTATTAATAAC |
| | TTAGTTAAAACAGAATTTACCAATGAAACTTTAGATAAAATACAGCAGA |
| | CACAAGACTTATTAAAAAAGATACCTAAGGATGTACTTGAAATTTATAG |
| | TGAATTAGGAGGAGAAATCTATTTTACAGATATAGATTTAGTAGAACAT |
| | AAGGAGTTACAAGATTTAAGTGAAGAAGAGAAAAATAGTATGAATAGT |
| | AGAGGTGAAAAAGTTCCGTTTGCATCCCGTTTTGTATTTGAAAAGAAAA |
| | GGGAAACACCTAAATTAATTATAAATATCAAAGATTATGCAATTAATAG |
| | TGAACAAAGTAAAGAAGTATATTATGAAATTGGAAAGGGGATTTCTCTT |
| | GATATTATAAGTAAGGATAAATCTCTAGATCCAGAGTTTTTAAATTTAA |
| | TTAAGAGTTTAAGTGATGATAGTGATAGTAGCGACCTTTTATTTAGTCA |
| | AAAATTTAAAGAGAAGCTAGAATTGAATAATAAAAGTATAGATATAAA |
| | TTTTATAAAAGAAAATTTAACTGAATTTCAGCATGCGTTTTCTTTAGCGT |
| | TTTCTTATTATTTTGCACCTGACCATAGAACGGTATTAGAGTTATATGCC |
| | CCCGACATGTTTGAGTATATGAATAAGTTAGAAAAAGGGGGATTTGAG |
| | AAAATAAGTGAAAGTTTGAAGAAAGAAGGTTAA (SEQ ID NO. 6) |

Immunization of Mice and Serum Collection. All mice in these studies were housed in the LARC facility of Texas Tech University Health Sciences Center El Paso. All studies were approved by the Institutional Animal Care and Use Committee. BALB/c mice (6-8 weeks) were purchased from Harlan Laboratories. Prior to intranasal immunization with vaccine candidates, mice were anesthetized via intraperitoneal (IP) injection of 100 µl of 80 mg/kg ketamine and 6 mg/kg xylazine. Groups of mice were then immunized via intranasal (IN) administration of 20-30 µl of the following: (1) 30 µg M2, (2) 30 µg EFn-M2, (3) 30 µg EFn-M2 with 60 µg PA, (4) 30 µg EFn-3×M2e-HA2, (5) 30 µg EFn-3×M2e-HA2 with 60 µg PA, or (6) PBS. Recombinant PA purified from *E. coli* was obtained from BEI Resources (Manassas, Va.). Mice were immunized at 0, 2, and 5 weeks. Mice were bled just prior to each immunization, and on week 7 via the submandibular method with 5 mm lancets. Additional studies were conducted in the same manner in wild-type, CD4 knockout (KO), and CD8 KO C57BL/6 mice (The Jackson Laboratory).

ELISA. ELISAs were performed to measure antigen-specific antibody responses in the sera of naïve and immunized mice. 96-well Corning® EIA/RIA plates (Corning, N.Y.) were coated with 1 µg/ml of recombinant antigens: M2, 3×M2e-HA2, EF, HA2, HA2-region peptides, or PA at 4° C. overnight. EF, HA, and HA2-region peptides were all obtained from BEI Resources. The plates were washed 5 times with PBS-T (PBS with 0.05% Tween-20) by the ImmunoWash™ 1575 microplate washer (Bio-Rad, Hercules, Calif.), then blocked with 1% bovine serum albumin (BSA) in PBS for 1 h at room temperature. Serum samples were diluted at 1:50 in 100 µl PBS-T per well and were incubated for 2 h at room temperature with rocking. After washing, secondary anti-mouse IgG-Fc, IgG1, and IgG2a were diluted at 1:10,000 in PBS-T and used at 100 µl/well. After 1 h incubation at room temperature with rocking, the plates were washed again. Bound antibody was detected using the p-nitrophenylphosphate phosphatase substrate system (KPL, Gaithersburg, Md.) as per manufacturer's protocol. Absorbances were measured at 405 nm using the PowereWave XS2 plate reader with Gen5 software (BioTek, Winooski, Vt.). Standard plates were coated with capture antibodies diluted at 1:500 in PBS-T:affinity purified anti-mouse IgG-Fc, IgG1, IgG2a, or IgA (Bethyl). Pooled sera from naïve BALB/c mice were serially diluted and used as the reference serum to develop isotype-specific standard curves. Secondary antibody was added as described for study plates and these plates were also developed and measured in the same way.

Influenza virus microneutralization assay. Microneutralization was performed as previously described (4) with some modifications. Briefly, mouse sera were heat-inactivated at 56° C. for 30 min, and two-fold serial dilutions were prepared. 50 µl of each dilution were added to one well of a microtiter plate and mixed with 50 µl ($2 \times 10^4$ pfu) of H1N1 influenza virus A/PR/8/34 (PR8, from VR-95, ATCC, Manassas, Va.). The plate was incubated for 1 h at 37° C., and 50 µl of the suspension was transferred onto MDCK cells. After 1 h incubation at 37° C. and 5% $CO_2$, the suspension with the virus and antibody was removed and 1% agarose in medium (MEM, 0.2% BSA, 1 µg/mL TPCK-trypsin) was added to each well. After 18-20 h, the agarose was removed and the cells were fixed with ethanol and stained with Coomassie Blue.

Lethal challenge with influenza viruses. Mice were challenged with H1N1 influenza virus PR8 two weeks after administration of the third vaccine dose. Each mouse was weighed first, then anesthetized with ketamine and xylazine, and administered intranasal (IN) with $2 \times 10^5$ PFU of live A/PR/8/34 in 40 µl. Mice were monitored for signs of illness and weighed for 21 days post-inoculation at the same time each day. Death was considered an endpoint for survival analysis. A different group of mice was challenged IN with $1 \times 10^5$ PFU of live A/CA/4/09 in 40 µl. Mice were monitored as before, and death, or 30% weight loss was considered an endpoint for survival analysis.

Anthrax lethal toxin neutralization assay. Toxin neutralization assays were performed as the inventors have previously described (20-23). Sera from mice were evaluated for the ability to neutralize anthrax LeTx. Serial dilutions of sera were incubated with 320 ng/ml recombinant LF purified from B. anthracis (BEI Resources) in PBS for 1 h. Next, recombinant PA purified from B. anthracis (BEI Resources) was added at 480 ng/ml and incubated for 1 h. The above solutions were then added to Raw 264.7 murine macrophage cells in 96-well plates at 100 µl/well and were incubated for 7 hours at 37° C. and 5% $CO_2$. In parallel, viable-cell control samples were incubated with 100 µl/well PBS. To assess cell viability, a thiazolyl blue tetrazolium bromide (MTT) colorimetric assay was employed as described by Twentyman et al (25), with some modification. Briefly, 20 µl of MTT was added to each well and incubated for 2 hours at 37° C. and 5% $CO_2$. Then, the medium was carefully removed and 200 µl/well of dimethyl sulfoxide was added to solubilize the formazan crystals formed. Absorbances were measured at 570 nm using the PowerWave XS2 plate reader with Gen5 software. Readings were normalized to viable-cell control samples for each study.

Lethal challenge with B. anthracis Sterne spores. A/J (6-8 weeks) mice were purchased from Jackson Laboratories. Groups of mice were intranasally immunized three times with 30 EFn-3xM2e-HA2 plus 60 µg PA, or subcutaneously (SC) immunized once with 50 spores from the Colorado Serum Company's anthrax spore vaccine (Denver, Colo.). Two weeks after the final immunizations, mice were SC challenged with $5 \times 10^4$-$1.8 \times 10^5$ spores. Mice were monitored for signs of illness and weighed for up to 14 days post-inoculation.

Analysis of T cell immune responses by intracellular cytokine staining. Mice were sacrificed via cervical dislocation and spleens were collected into microcentrifuge tubes containing DMEM medium supplemented with 10% heat-inactivated fetal bovine serum, 100 U/ml penicillin, and 100 µg/ml streptomycin (DMEM-10). Spleen cells were mechanically isolated by straining through 100 µm nylon mesh cell strainers. Red blood cells were removed using ACK lysis buffer followed by a washing step. The splenic mononuclear cells were used for studies at $2 \times 10^6$ cells/ml in 0.5 ml DMEM-10/well. These cells were left untreated or stimulated with 10 µg/ml of the following antigens: phytohaemagluttinin (PHA, Sigma-Aldrich, St. Louis, Mo.), M2, 3xM2e-HA2, PA, M2e region peptides from A/New York/348/03 (H1N1) M2 peptide array (NR-2614, BEI Resources), HA2 region peptides from A/California/04/2009 (H1N1) HA peptide array (NR-19244, BEI Resources), or recombinant EF (NR-13413, BEI Resources). GolgiStop transport inhibitor (BD Biosciences, San Jose, Calif.) was added to spleen cell cultures for the last 4 h of stimulation. After stimulation, cells were harvested and washed in staining buffer (PBS+2% FBS) with centrifugation at 800×g for 5 min. Cells were resuspended in BD FACS lysis buffer diluted in water at 1:10 and incubated for 10 min at room temperature. After washing, the cells were resuspended in 0.5 ml PBS, and then 0.5 ml BD Perm2 buffer diluted in water at 1:10 was added for 10 min at room temperature. After washing, the cell samples were stained for 30 min with antibodies targeting T cell markers and intracellular cytokines (Table II). All antibodies were purchased from BD Biosciences with the exception of anti-mouse CD25 and anti-mouse Foxp3 which were purchased from Affymetrix, eBioscience. After washing, the samples were fixed in 2% formaldehyde solution. Foxp3 transcription factor staining was performed according to manufacturer instructions (Affymetrix, eBioscience). The CD4+/CD25+ and CD4+/CD25+/Foxp3+ cell populations were normalized by dividing the mean of stimulated cells by the mean of unstimulated cells. The samples were measured using a BD FACSCanto II flowcytometer (BD Biosciences, San Jose, Calif.), and 50,000 to 100,000 total events per sample were collected. The acquired data were then analyzed with FlowJo v10 software (FlowJo, Ashland, Oreg.).

TABLE II

T cell staining for FACS

| Marker | Fluorochrome |
| --- | --- |
| IL-6 | AlexaFluor 488 |
| IL-4 | PE |
| CD25 | PE-Texas Red |
| IL-17 | PerCP-Cy5.5 |
| TNF-α | PE-Cy7 |
| IFN-γ | APC |
| CD3 | AlexaFluor 700 |
| CD4 | Pacific Blue |
| CD8 | V500 |

T-cell proliferation assay. Splenocytes ($2 \times 10^5$ cells per well of a 96-well plate) from vaccinated mice or non-vaccinated control mice were stimulated with linear synthetic peptides of HA2 (10 µg/ml) or with phorbol myristate acetate (PMA) as a positive control for 3 days. T cells were analyzed for ATP content with the CellTiter-Glo luminescent cell viability assay (Promega Corporation, Madison, Wis.). Stimulation indices were determined by dividing the mean of relative luminescent units of stimulated cultures by that of relevant non-stimulated controls.

Tetramers and staining. The following tetramers were obtained through the NIH Tetramer Core Facility at Emory University (Atlanta, Ga.): I-A(d)/SLLTEVETPIRNEWGS (SEQ ID NO.: 7) and H-2K(d)/VETPIRNEW (SEQ ID NO.:

8). The MHC Class II tetramer was available as a pre-made reagent, and was labeled with PE. The latter tetramer was designed based on previous studies that identified VETPIRNEW (SEQ ID NO.: 8) as a MHC class I influenza epitope in mice and humans (26, 27). This peptide was synthesized by GenScript and shipped to the NIH Tetramer Core Facility for synthesis of tetramer, labeled with APC. For tetramer staining studies, mice were sacrificed via cervical dislocation and spleens were collected into microcentrifuge tubes containing DMEM-10. Spleen cells were mechanically isolated by straining through 100 μm nylon mesh cell strainers. Red blood cells were removed using ACK lysis buffer followed by a washing step: cells were centrifuged at 1500 RPM for 5 min at 4° C. using Allegra X-12R equipment (Beckman Coulter, Miami, Fla.). The splenic mononuclear cells were used for studies at $1\times10^6$ cells/ml in 0.1 ml DMEM-10 per well. For MHC class II studies, cells were stained with 1 μg tetramer for 3 h at 37° C. The collected samples were washed in staining buffer with centrifugation at 1500 RPM for 5 min. Samples were then stained with anti-mouse CD4-APC and CD3-Alexa Fluor 700 (BD Biosciences, San Jose, Calif.) for 30 min at room temperature in the dark. For MHC class I studies, cells were stained with 1:100 dilution of tetramer for 30 min at room temperature. After washing, these samples were stained with anti-mouse CD8-PE and CD3-FITC (BD Biosciences) for 30 min at room temperature in the dark. All samples were washed once more and resuspended in 300 μl 2% formaldehyde in PBS. 100,000 total events were acquired using a Gallios cytometer (Beckmann-Coulter, Miami, Fla.) and data were analyzed using FlowJo v10 software.

Statistical analysis. GraphPad Prism 6 software was used to perform numerical and statistical analyses including: 1) calculations of mean and error; 2) Kaplan-Meier survival analyses for challenge studies; 3) two-way, two-tail ANOVA with post-tests for T cell stimulation studies; and 4) Student's t-tests. Differences were defined as statistically significant when $p<0.05$.

Figure 1B:
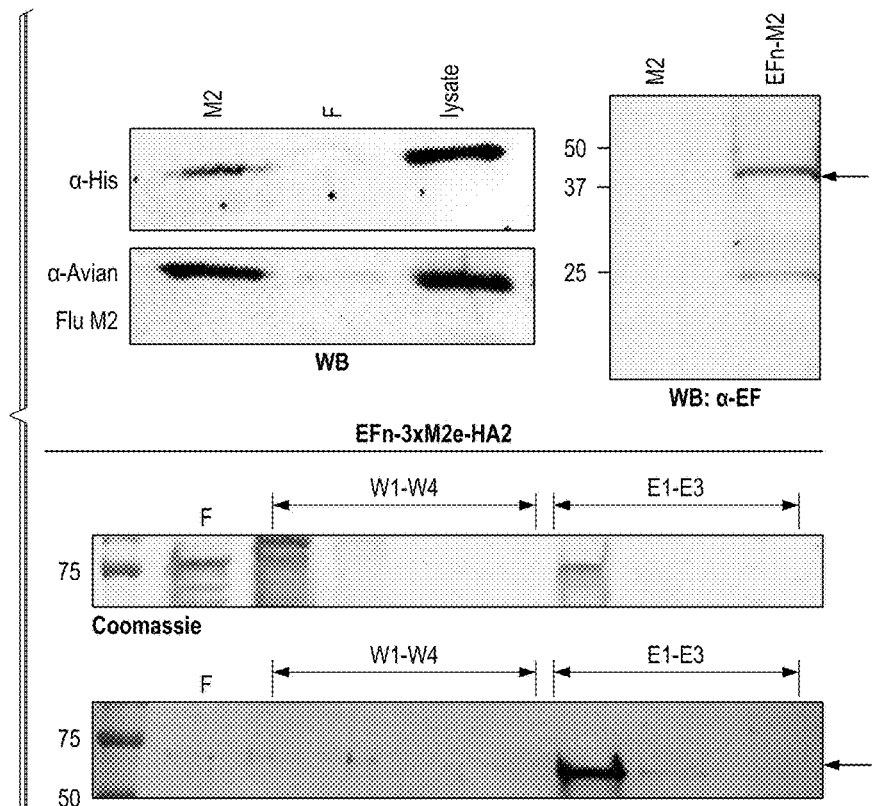

Vaccine antigen design and influenza antigen-specific humoral immunity. The present inventors designed a broad-spectrum vaccine for influenza and anthrax using the relatively conserved M2 and HA2 of influenza A virus as universal antigens delivered by detoxified anthrax edema toxin. Thus, the inventors designed (Table I & FIG. 1A) and purified (FIG. 1B) an array of recombinant proteins in *E. coli* to be used for varying vaccine formulations. Successful confirmation and expression of these proteins were confirmed by Western Blot analysis. Representative blots are shown in FIG. 1B, confirming the reactivity of the vaccine candidates with anti-His, anti-Avian M2, and anti-EF antibodies.

Figure 2A:
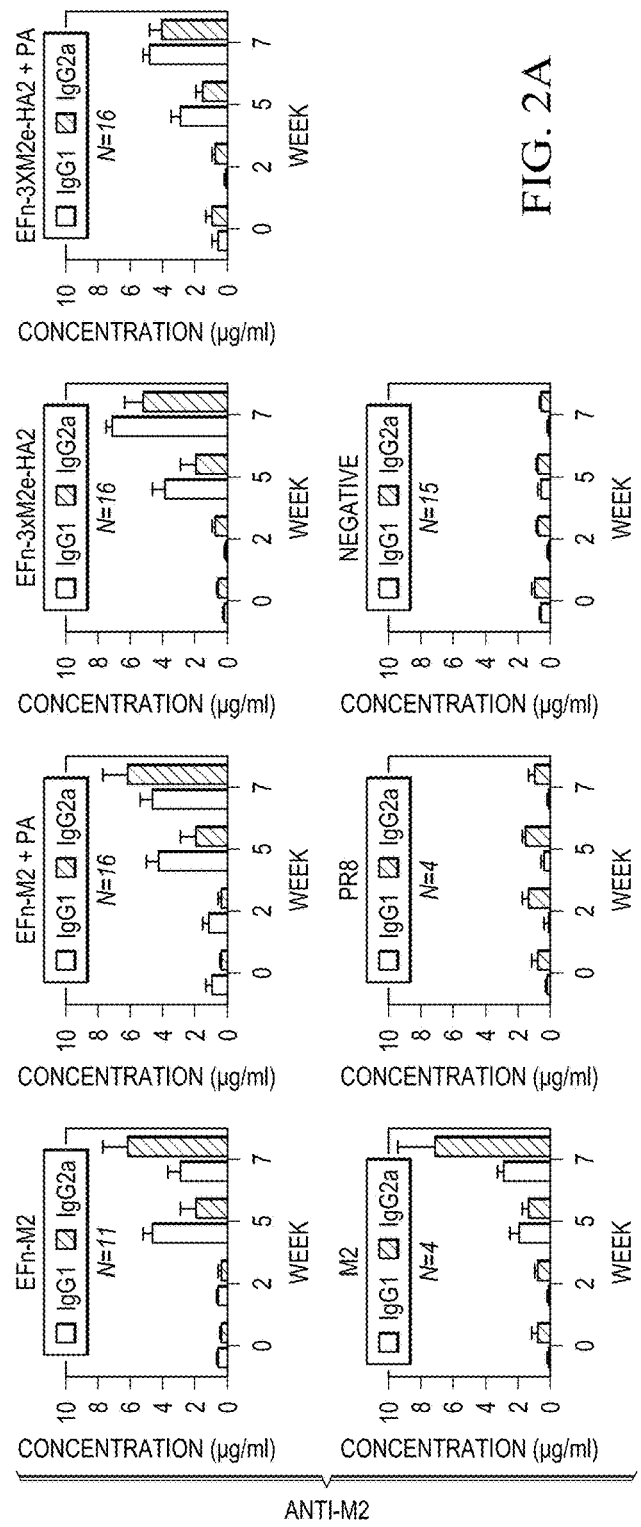
Figure 2B:
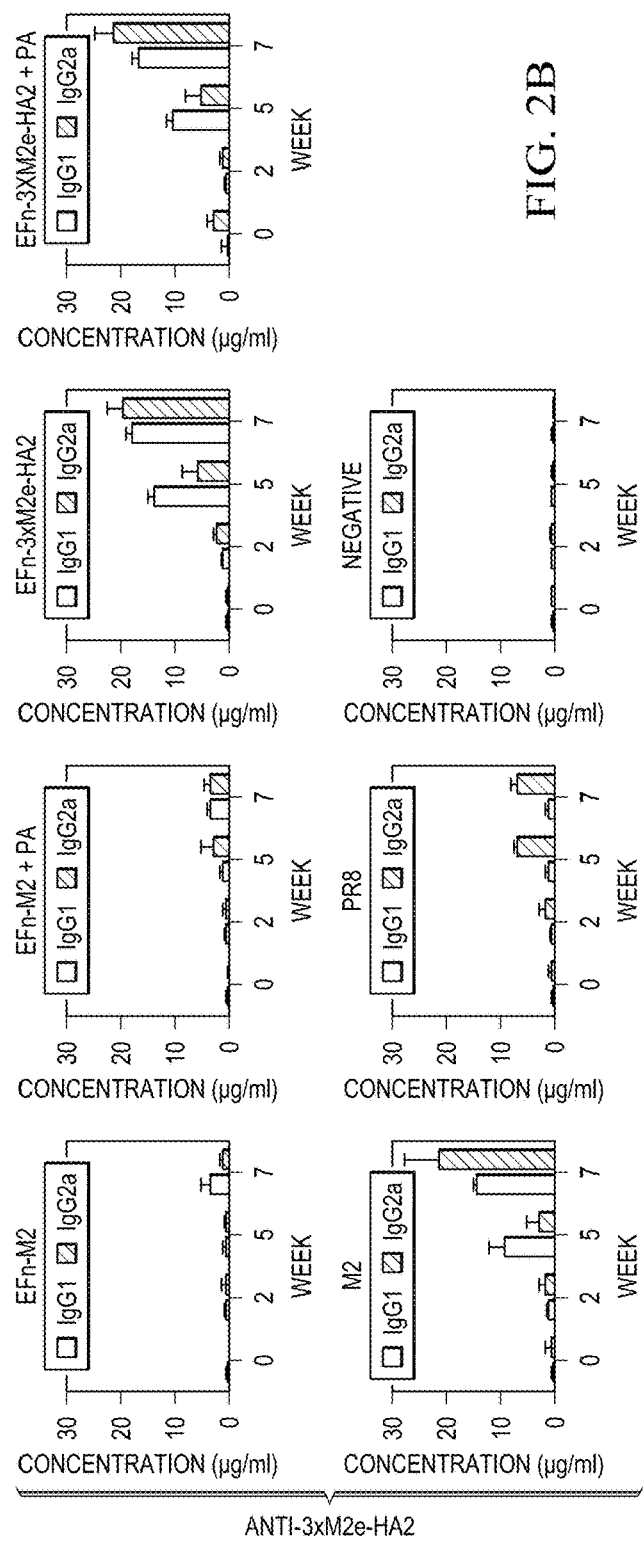
Figures 2C, 3A:
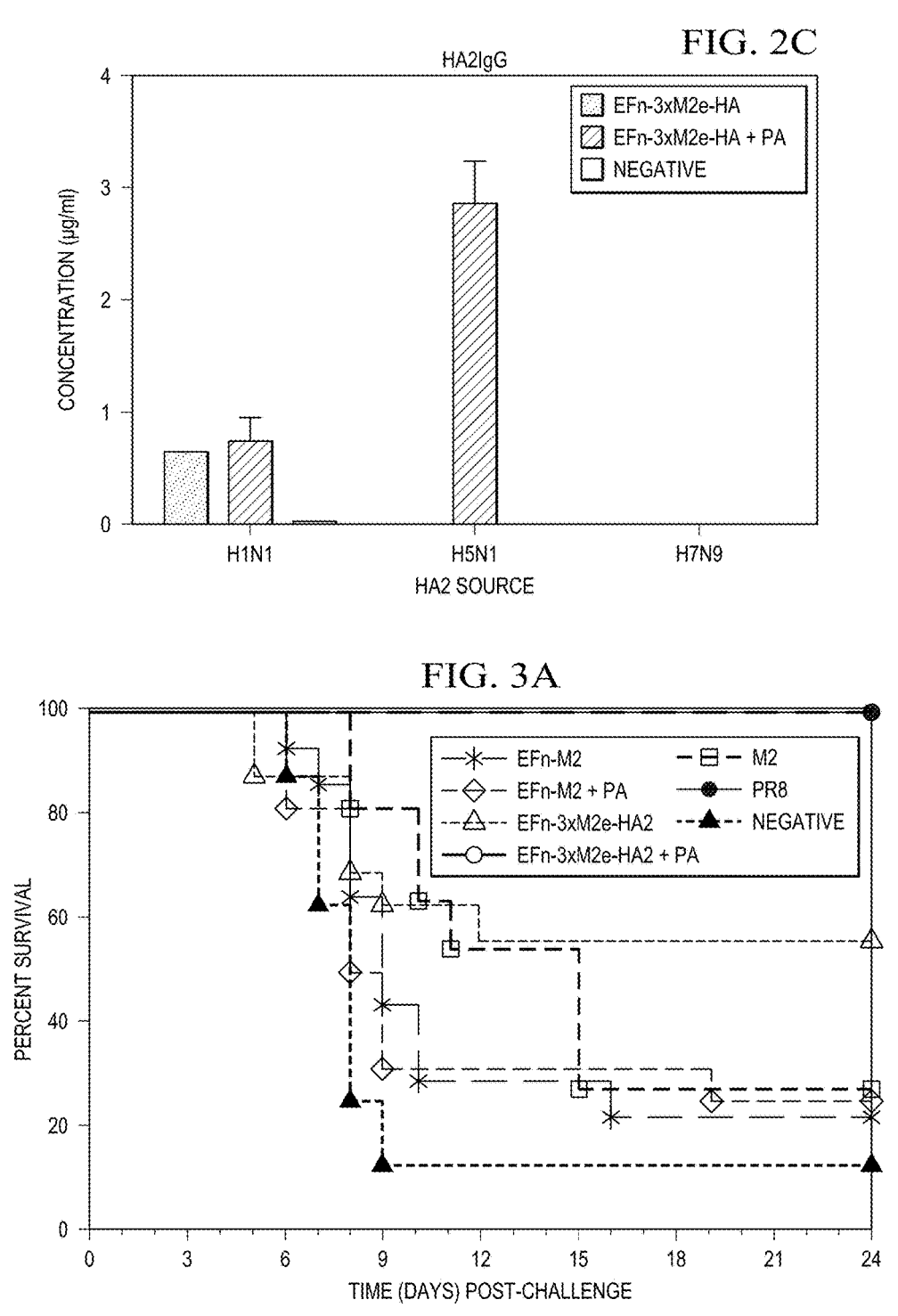

Immunized mice were evaluated for systemic antibody responses against recombinant M2 and 3×M2e-HA2 antigens. Results in FIG. 2A showed that immunization with all vaccine formulations tested (M2, EFn-M2, EFn-M2 plus PA, EFn-3×M2e-HA2, and EFn-3×M2e-HA2 plus PA) stimulated strong reactivity against avian M2 by IgG1 and IgG2a antibodies. In addition, results in FIG. 2B showed that immunization with EFn-3×M2e-HA2 or EFn-3×M2e-HA2 plus PA induced high levels of serum IgG1 and IgG2a antibodies against recombinant 3×M2e-HA2. Sera from mice immunized with EFn-M2 or EFn-M2 plus PA also reacted with recombinant 3×M2e-HA2 protein, but to lesser extents. Of interest, mice immunized with recombinant, full-length M2 from avian influenza A virus had robust IgG1 and IgG2a responses similar to mice immunized with EFn-3×M2e-HA2 or EFn-3×M2e-HA2 plus PA. Moreover, inclusion of the centralized HA2 portion in the vaccine formulation elicited specific antibodies against HA2-region peptides from A/California/7/2009 (H1N1) virus (FIG. 2C). However, only the EFn-3×M2e-HA2 plus PA formulation elicited antibodies reactive with full-length HA protein from A/Vietnam/1203/2004 (H5N1).

Figure 3B:
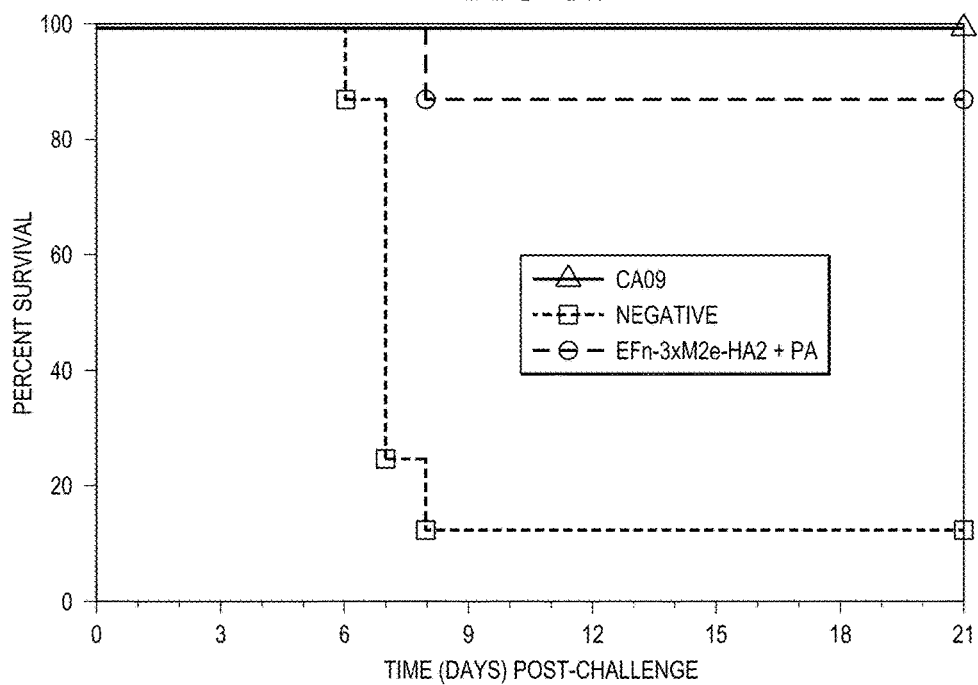
Figure 3C:
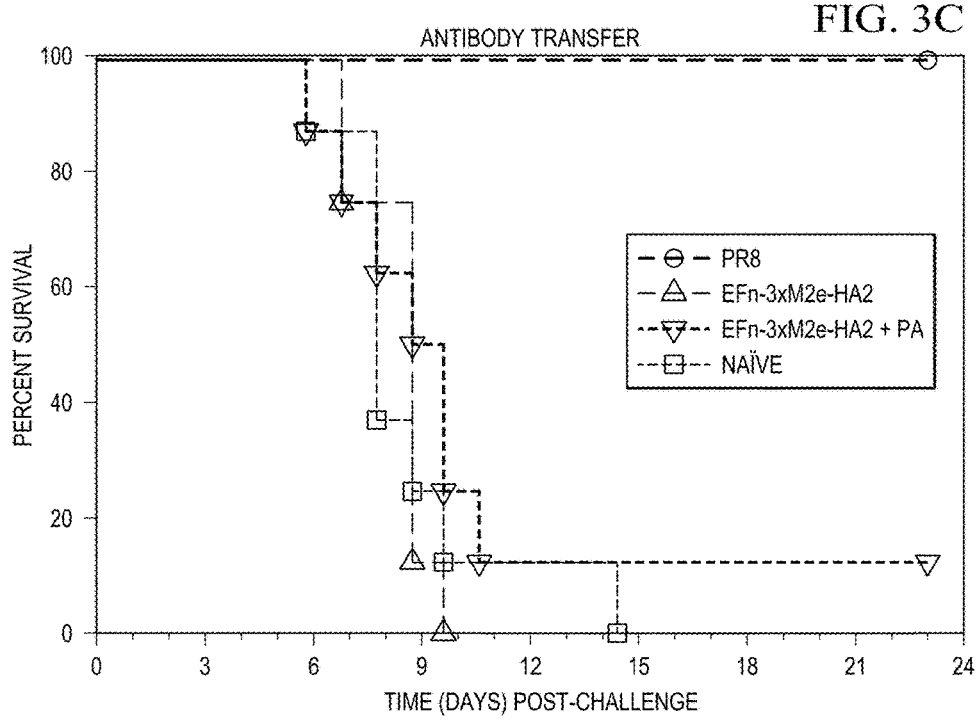

Protection against influenza viral challenge. While all vaccine candidates elicited potent humoral responses, only immunizations with EFn-3×M2e-HA2 plus PA (3 doses) reproducibly protected 100% of mice against PR8 influenza virus challenge, while other immunizations provided less exciting degrees of protection (FIG. 3A). As expected, all mice were protected when immunized with a one-time, low dose of PR8 at 50 pfu per mouse, with no weight loss associated with challenge. In addition, some protection was observed in mice immunized with EFn-3×M2e-HA2 (56%) (FIG. 3A). Next, protection by EFn-3×M2e-HA2 plus PA was tested against challenge with CA09 virus. Immunization with EFn-3×M2e-HA2 plus PA offered a protection rate of 88%, while immunization with a one-time, 50 pfu dose of CA09 was 100% protective as expected (FIG. 3B). Next, the inventors tested if sera from the EFn-3×M2e-HA2 plus PA would protect naïve mice from lethal challenge with PR8 virus. Next, 200 μl of naïve or immune sera was transferred to naïve mice via intraperitoneal injection one day prior to challenge with PR8 virus. Only serum from mice vaccinated with a low-dose of PR8 virus transferred protective immunity against lethal challenge with PR8 virus (FIG. 3C). Neither naïve sera, nor sera from mice vaccinated with EFn-3×M2e-HA2 with or without PA protected mice against lethal challenge with PR8 virus. This indicated that protective immunity by the EFn-3×M2e-HA2+PA vaccine was not solely dependent on vaccine antigen-specific antibody responses. Two additional studies employing passive transfer of naïve or immune sera to mice via intravenous or intraperitoneal injections one day prior to challenge yielded the same results (data not shown). Furthermore, influenza virus neutralizing antibody titers in immune sera were measured by influenza virus microneutralization assay using MDCK cells. The results showed that immunization with EFn-3×M2e-HA2 plus PA or without PA did not elicit neutralizing antibody responses against PR8 influenza virus (neutralization titers <10). In contrast, sera from control mice vaccinated with PR8 virus had virus neutralization titer of ≥2560 (Table III).

TABLE III

Micro-neutralization assay: neutralizing antibody titers against PR8 influenza virus

| Groups | Titers (2 weeks after the 3$^{rd}$ immunization) |
|---|---|
| EFn-3 × M2e-HA2/PA | <10 |
| EFn-3 × M2e-HA2 | <10 |
| PR8 | ≥2560 |
| PBS | <10 |

Figures 4C, 4D:
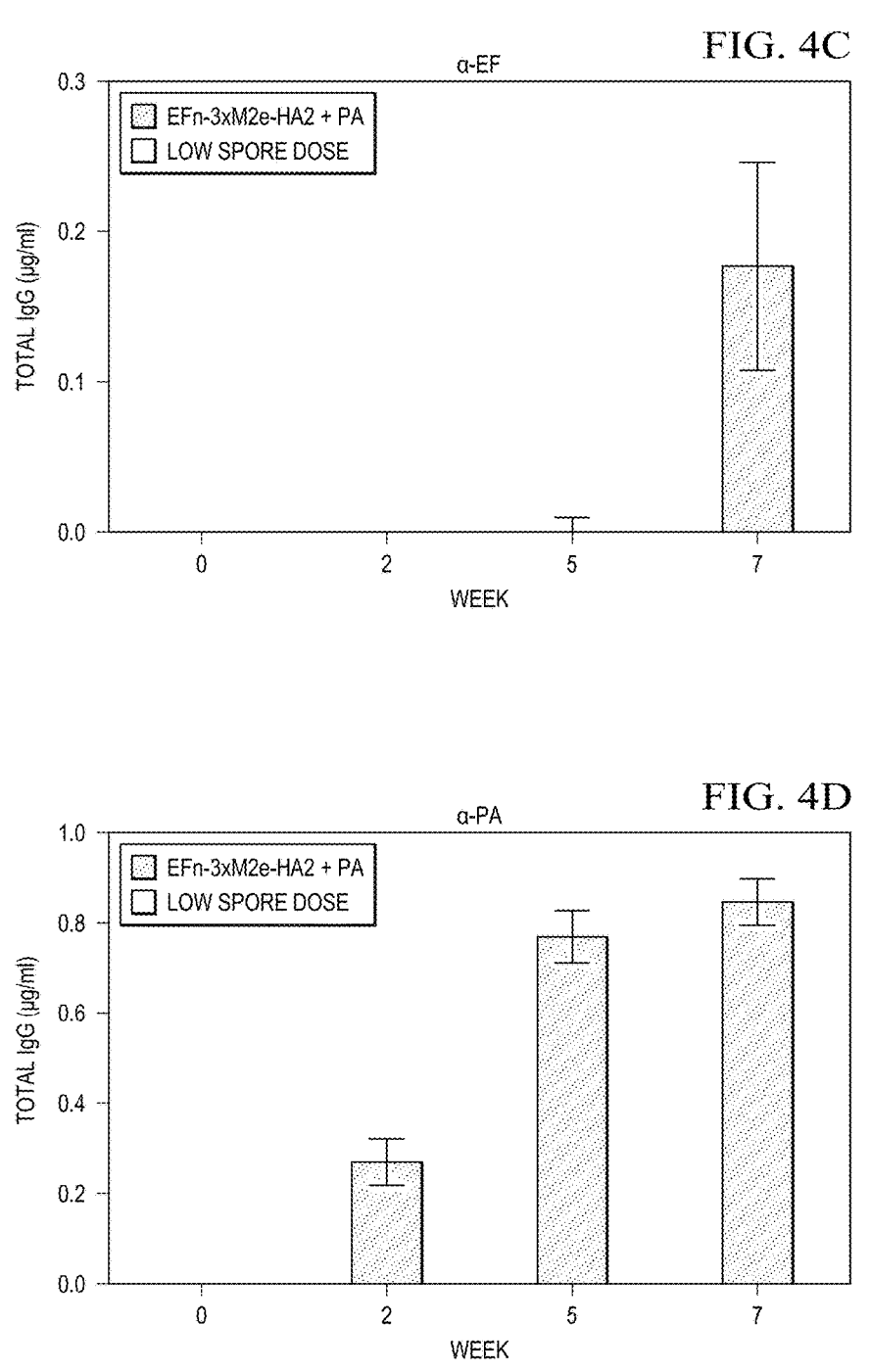
Figure 4E:
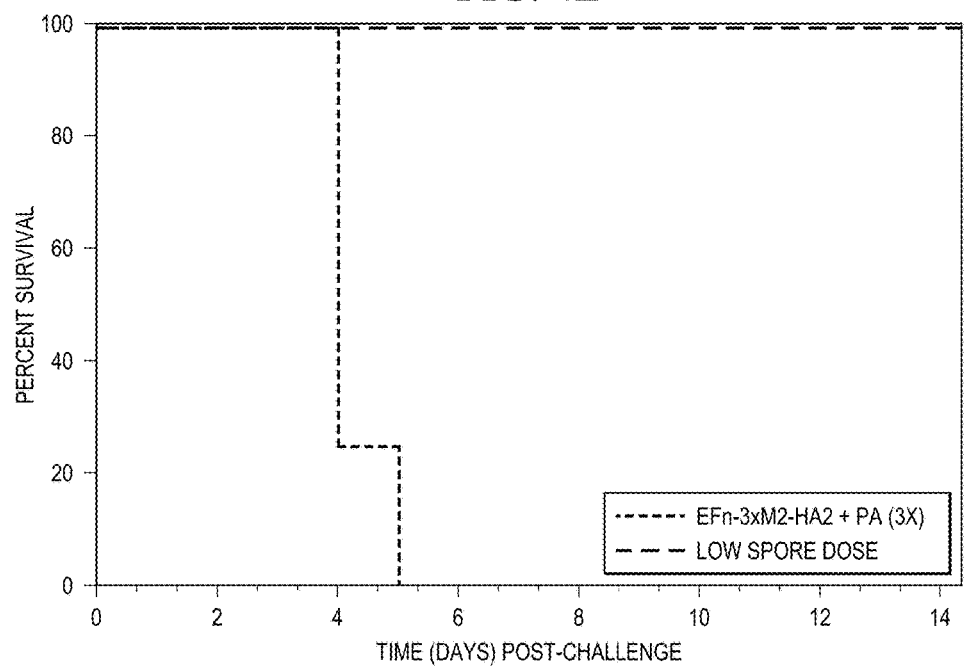
Figure 4F:
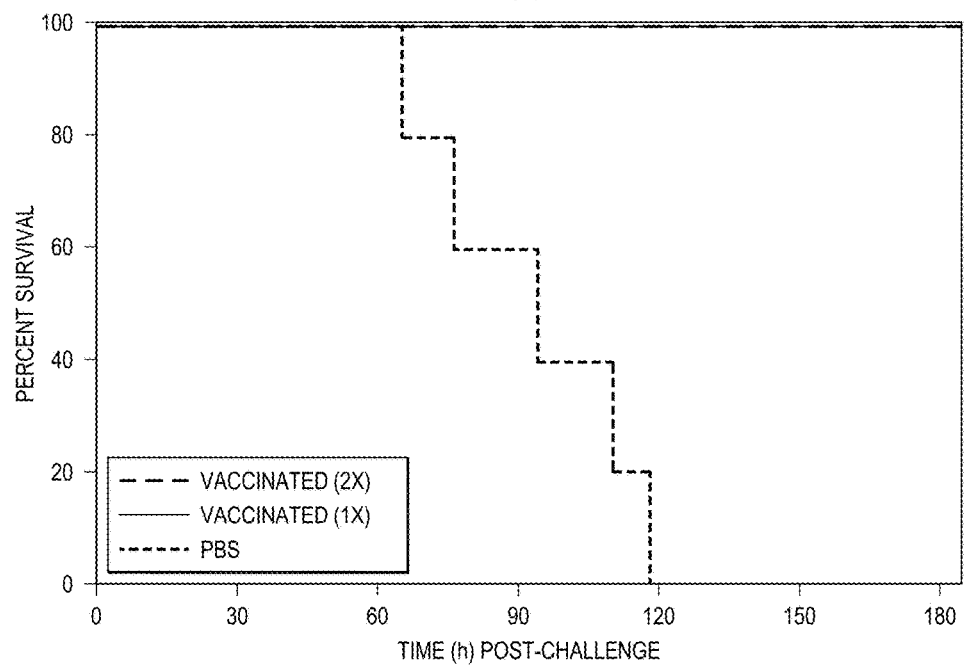

Immunity against anthrax in mice immunized with EFn-3×M2e-HA2 plus PA. After establishing that the vaccine candidates elicited specific immunity against influenza antigens, it was next tested if specific immunity against anthrax toxins were also developed. Therefore, the inventors used their experience in performing anthrax toxin assays and neutralization assays to evaluate the ability of these sera to neutralize anthrax LeTx. Sera from BALB/c or A/J mice immunized with EFn-3×M2e-HA2 plus PA completely protected Raw 264.7 mouse macrophages from LeTx even at dilutions of 1:20 to 1:800 (FIGS. 4A & B). Even at a 1:6400 dilution, sera from A/J mice immunized with EFn-3×M2e-HA2 plus PA provided strong protection, and challenged cells maintained 78% viability (FIG. 4B). In contrast, sera from naïve mice or from mice immunized with EFn-3×M2e-HA2 were not protective at any dilution. Next, the inventors confirmed the anthrax toxin-specific antibody responses in A/J mice by ELISA. EFn-3×M2e-HA2 plus PA induced systemic IgG responses against anthrax EF and PA proteins as measured by ELISA (FIGS. 4C & D). The response to PA occurred earlier and was stronger than the response to EF (0.8 µg/ml to 0.2 µg/ml, respectively). Protective immunity was then assessed in mice challenged with $B$. $anthracis$ Sterne spores. Mice immunized with 3 doses of EFn-3× M2e-HA2 plus PA (N=8) were all protected against challenge with $5 \times 10^4$ spores, while animals immunized once with 50 spores via subcutaneous injection died by day 5 (FIG. 4E). 100% of mice were also protected against challenge after receiving one or two doses of EFn-3×M2e-HA2 plus PA, despite an increased challenge dose of $1.8 \times 10^5$ spores (FIG. 4F). Vaccination with 50 spores administered via subcutaneous injection did not provide any measurable immunity against anthrax (FIGS. 4C-E). Thus, the EFn-3× M2e-HA2 plus PA formulation induced anthrax toxin neutralizing antibodies that potentially contributed to protecting mice from lethal challenge with $B$. $anthracis$ Sterne spores.

T cell immunity. A more complete picture of how the vaccine formulation provides protection against influenza challenge, vaccine-antigen specific T responses by various methods were determined. First, antigen-stimulated responses were measured by FACS. In mice immunized with EFn-3×M2e-HA2 plus PA, there were significant increases in the percentages of CD4+/CD25+/FoxP3+ Treg cells (28) in response to PA or M2e peptides (FIGS. 5A and 5B) as compared to control mice. Upon PA stimulation, a significant difference in Treg cells was found between mice vaccinated with EFn-3×M2e-HA2 plus PA and EFn-3×M2e-HA2 alone. PMA were used as positive control for stimulation, and PMA also stimulated an increase in the percentage of Treg cells (FIG. 5A). However, recombinant EF and HA2 peptides did not induce any Treg response (data not shown). To study the T cell responses induced by HA2, the inventors preformed cell proliferation assay using linear peptides of the chimeric HA2. None of the peptides induced proliferation of spleen cells from immunized mice or control mice (data not shown). Vaccine antigen-specific IL-2, IL-4, IL-6, IL-17, TNF-α, or IFN-γ positive T cell responses were also not detected by FACS (data not shown). ELISPOT analyses following 2-day stimulations with 3×M2e-HA2 confirmed that there were no significant inductions of IL-4 or IFN-γ (data not shown). These results suggested that EFn-3×M2e-HA2 plus PA vaccine taught herein triggers an immune-suppressive Treg response, in response to stimulation with M2e or PA.

Figure 6A:
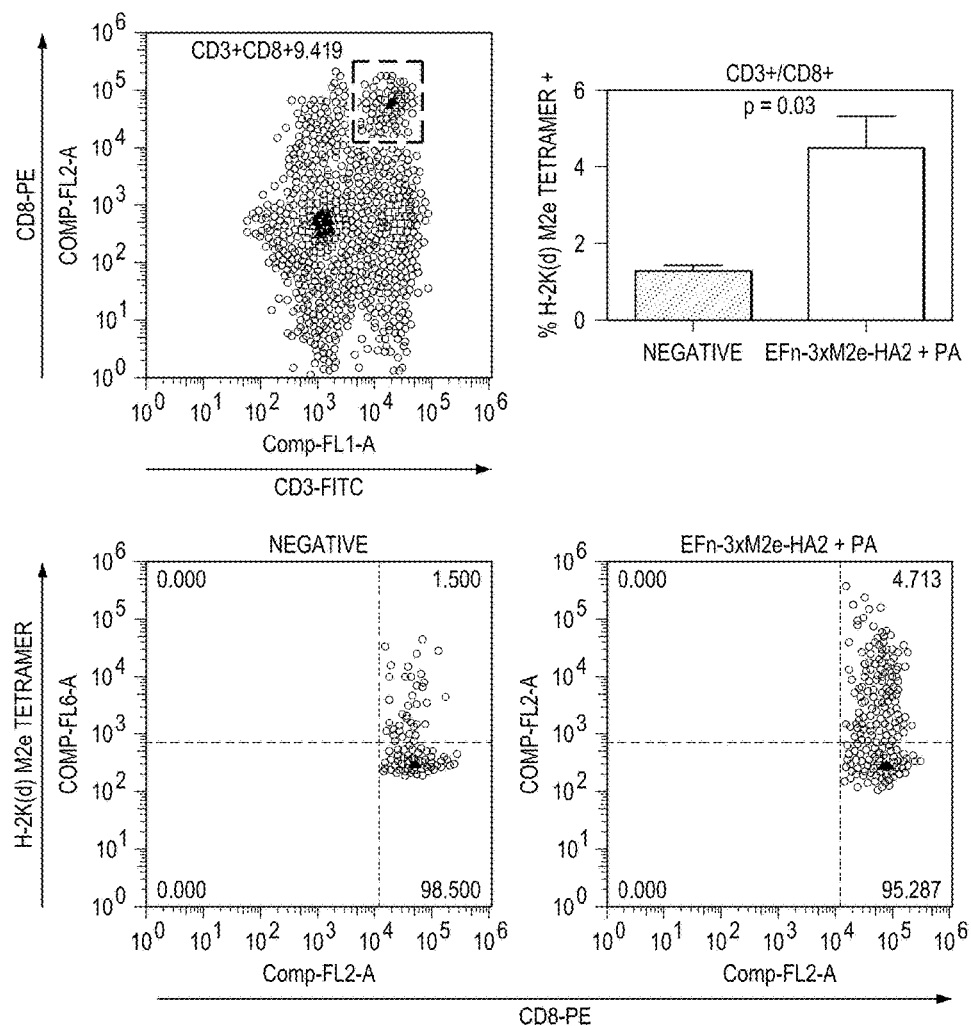
Figure 6B:
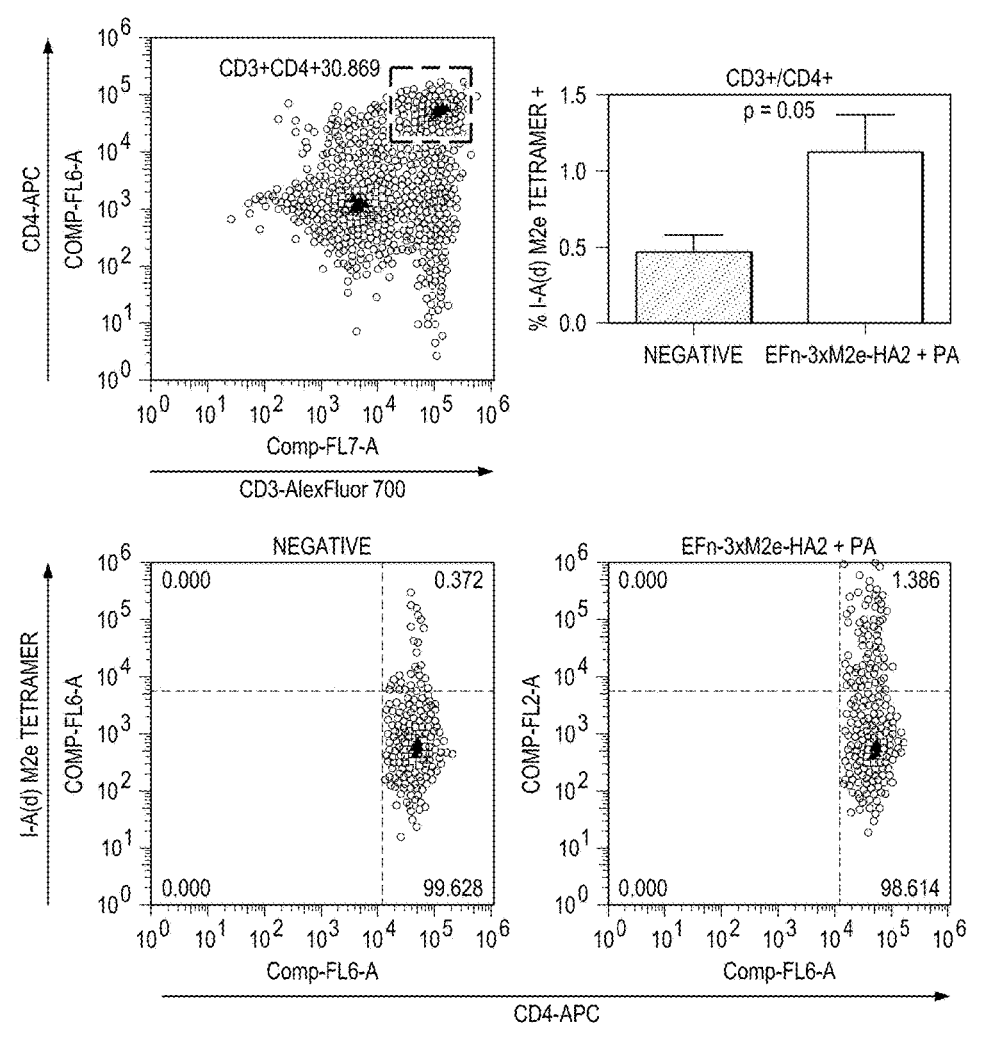

To decipher what additional cellular immunities were elicited by the vaccine candidate, tetramer-staining was used as a more sensitive approach to detect influenza-antigen specific T responses. The $M2_{7-15}$ VETPIRNEW (SEQ ID NO.: 8) epitope has been identified as a HLA-B27 and HLA-B44 epitope in humans (27), and H-2Kd-restricted epitope in mice (26). Thus, this peptide was to use in probing influenza-specific responses. For completion, a class II, restricted M2e-epitope tetramer that was already available from the NIH tetramer core facility was also used. Using this methodology, it was found that immunization with EFn-3× M2e-HA2 plus PA elicited specific, M2e-epitope CD8 (4.4%, FIG. 6A) and cell CD4 (1.1%, FIG. 6B) T responses based on positive tetramer-binding. Furthermore, T cell responses by immunized mice were statistically significant from naïve mice as determined by Student's, two-tailed t-tests, where p≤0.05 was considered significant.

Figure 7A:
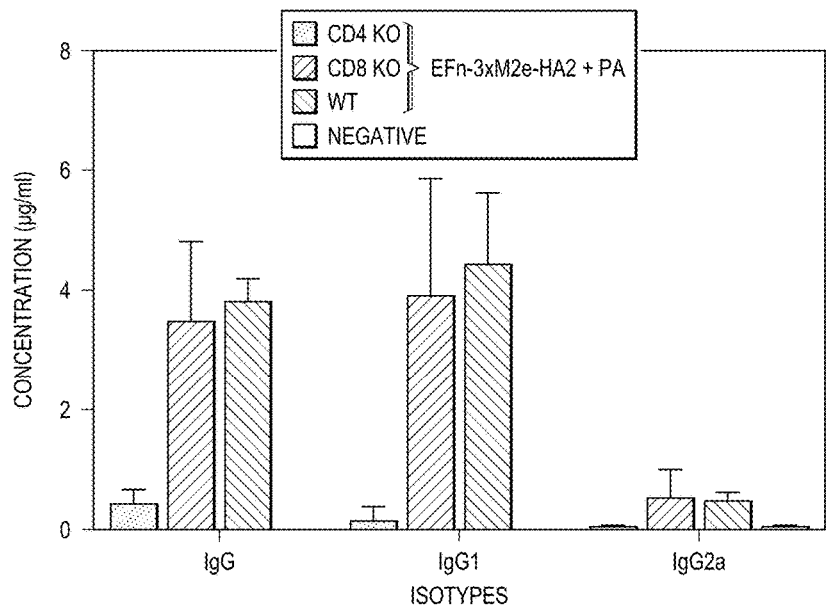
FIGS. 7A and 7B show the role of humoral and T cell immunities in survival of vaccinated mice. Wild type (WT), CD4 knockout (KO), or CD8 KO C5BL/6 mice were vaccinated with PBS, or EFn-3×M2e-HA2+PA. N=8 for all groups, except CD8 KO+vaccine where N=7. The mice were challenged with PR8 virus as before and (FIG. 7A) Antibody responses against recombinant 3×M2e-HA2 were measured by ELISA and (FIG. 7B) Kaplan-Meier survival curves are shown.
Figure 7B:
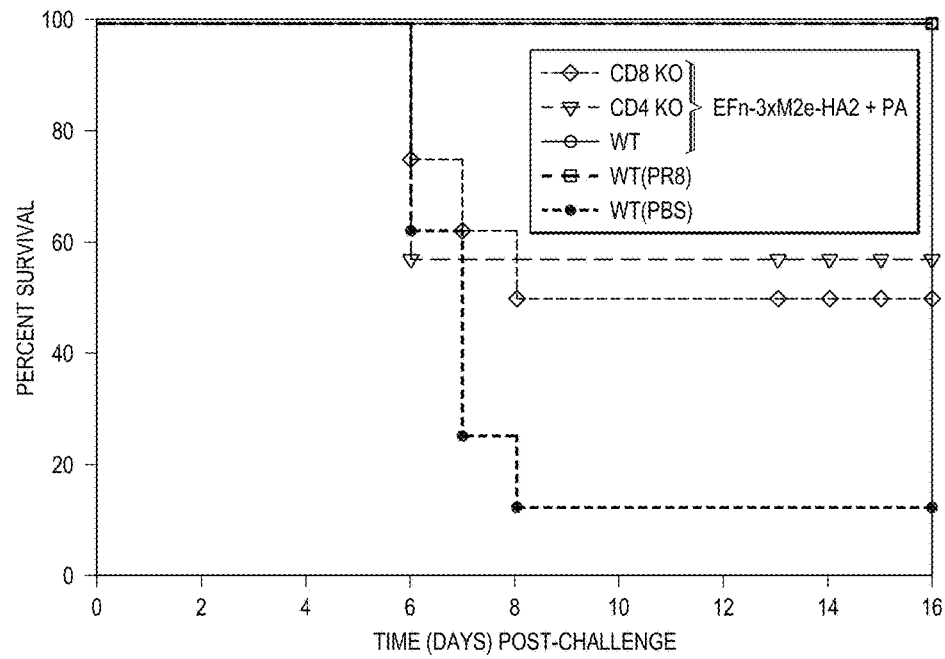

In addition, to show that T-cell immunities were important in eliciting protection by the vaccine of the present invention against lethal influenza challenge, wild-type, CD4 KO, and CD8 KO C5BL/6 mice were vaccinated with PBS, PR8, or EFn-3×M2e-HA2+PA as before for BALB/c mice. Serum antibody responses against 3×M2e-HA2 were evaluated by ELISA. As shown in FIG. 7A, vaccinated CD4 KO mice produced low titers of antigen-specific IgG, IgG1, and Ig2a antibody responses against 3×M2e-HA2, while vaccinated CD8 KO and C5BL/6 WT mice showed strong and equivalent antibody responses. These mice were then challenged with PR8 virus. Results showed that wild-type mice immunized with a low-dose of PR8 virus are completely protected from weight loss and death (FIG. 7B). Wild-type mice immunized with EFn-3×M2e-HA2 plus PA showed 100% survival against PR8 challenge, albeit some weight loss was observed. In contrast, the rate of protection by the EFn-3× M2e-HA2+PA vaccine candidate in CD4 (57%) or CD8 KO (50%) mice greatly diminished.

The EFn-3×M2e-HA2 plus PA vaccine formulation addresses the need for adequate vaccine strategies against influenza viruses and anthrax. Seasonal influenza virus epidemics account for 3-5 million cases of severe illness and between 250,000-500,000 deaths worldwide (29). The influenza viruses that currently circulate in humans are mainly influenza A H1N1, H3N2, and B influenza viruses. Since influenza viruses are constantly mutating, seasonal, trivalent-strain influenza virus vaccines must be produced annually. The 2009 H1N1 influenza virus pandemic demonstrated the need for a broad-range influenza vaccine. Furthermore, there is a threat that avian H5N1, H7N3 and H9N2 may adapt to humans in the near future. Cross-species transmissions of avian influenza viruses have already been shown to occur in pigs, horses, harbor seals, whales, and minks. Outbreaks of severe disease and mortality have been observed in these mammals (30). As production of influenza vaccines is time-consuming, the availability of an effective vaccine against a highly infectious, non-vaccine virus significantly lags. Thus, influenza viruses are a constant public health threat. The limitations of the current annual influenza vaccine has led to ongoing efforts to develop a vaccine that targets ubiquitous portions of the influenza virus so that the coverage of vaccination can (1) persist for multiple years and (2) provide broad, cross-strain protection.

EFn-M2 and EFn-M2 plus PA formulations produced antibodies that reacted with avian M2 and cross-reacted with 3×M2e-HA2 antigens, but it was disappointing that these responses were not more robust than immunizations with avian M2 alone. In this context, inclusion of EFn or PA in the formulation did not enhance immunogenicity of M2 as desired. These formulations were also not protective against lethal infection with PR8 virus. On the other hand, EFn-3× M2e-HA2 and EFn-3×M2e-HA2 plus PA formulations induced stronger antibody responses against influenza 3×M2e-HA2, with strong antibody cross-reactivity to avian M2 and H1N1 HA2. The antibody responses induced by EFn-3×M2e-HA2 and EFn-3×M2e-HA2 plus PA were similar; however, vaccination with EFn-3×M2e-HA2 was only 56% protective against influenza challenge. In contrast, vaccination with EFn-3×M2e-HA2 plus PA protected 100% of mice from challenge with PR8 virus and 88% of mice from challenge with CA09 virus. Based on the inventors' previous studies (31), the inventors predicted that this formulation can also protect against H3N2 viruses. The inventors further predict, based on cross-reactive antibody responses to H5N1 avian M2 and HA2, that this vaccine may also protect against H5N1 viruses. Some studies have been demonstrated that human monoclonal antibodies recognize conserve epitopes of HA2. Depending on their concentration, these monoclonal antibodies can neutralize the virus and protect mice from lethal challenge of influenza B viruses (32). However, it is important to note in current study, that antigen-specific antibodies elicited by vaccination with the vaccine could not neutralize the influenza virus as demonstrated in the passive antibody transfer and virus micro-neutralization studies. These results were not unreasonable, since it has been shown that antibodies against M2 or HA2 do not have direct virus neutralizing or hemagglutinin inhibition activity (5, 33-35), but somehow aid in clearing viral loads faster and inhibit the viral life cycle. Thus, the inventors reasoned that T cell responses elicited by the vaccine formulation taught herein plays a major role in protection.

The present inventors found that the EFn-3×M2e-HA2 plus PA formulation induced CD4 and CD8 responses against epitopes within the highly-conserved M2e region, and that CD4 and CD8 responses are important for survival against lethal challenge. Infections with influenza A virus stimulate strong CD4+ and cytotoxic CD8+ responses for viral clearance, but these host responses can induce significant immunopathology and even death (36). Thus, it is possible that in response to viral challenge, mice immunized with EFn-3×M2e-HA2 plus PA may launch CD4+ and CD8+ responses for viral clearance, but also promote regulation of these responses by influenza-specific Treg cells. These Tregs may be essential in reducing illness associated with inflammatory responses against influenza viral infection. It is known that in response to influenza viral infection, antigen-specific Treg cells migrate to lungs (37, 38). The Treg response to influenza infection occurs even quicker during a secondary infection, with increased Treg accumulation occurring faster in the lung draining lymph nodes and lung parenchyma (37). The influenza-specific Treg response precedes the effector T cell response (36, 37), and suppresses it by inhibiting proliferation of CD4+ and CD8+ cells (36-38). Another interpretation of these results is that induction of Treg responses may not be ideal, and thus, Treg epitopes should be evaluated and targeted for deletion as a means to improve this vaccine (39). This is beyond the magnitude of this work, but could be revisited in a future study.

It is possible that use of the detoxified anthrax toxins in this system may skew the immune responses. Activation of T cell function is compromised by EdTx and LeTx; secretions of various cytokines are inhibited (40). Edema toxin inhibits secretion of IL-17, TNF-α, and IFN-γ by stimulated T cells (40). However, EFn in the vaccine formulations should be devoid of enzymatic activity and thus, nontoxic when bound to PA. Furthermore, stimulation with full-length EF did not elicit a Treg response, while PA did. Thus, it is possible that PA is able to induce Treg responses. Although the immunization with the vaccine induces antibody responses against HA2 of 2 different strains of influenza virus, the inventors did not find any stimulation of T cells by the HA2 peptides. It may be that HA2 in the vaccine mainly induces antibody responses, which may target and prevent the membrane fusion process (41). Ultimately, the combination of humoral and T cellular immunities elicited by the EFn-3×M2e-HA2 plus PA formulation are protective against influenza virus.

The EFn-3×M2e-HA2 plus PA vaccine also elicited potent, neutralizing antibody responses against anthrax toxins. These responses contributed to the protection observed in mice challenged with anthrax spores. The immunized mice all survived, without any signs of illness or discomfort noted. Thus, the vaccine offered complete protection against anthrax disease. In short, the dual vaccine formulation described above provides complete protection against two very important public health concerns.

```
Amino Acid Sequences -
HA2 amino acid sequence -
                                           (SEQ ID NO: 9)
GLFGAIAGGYHHQNEQGSGYAADQKSTQNAIDGITNKVNSVIEKMNTQFT

AVGKEFNKLEKRIENLNKKVDDGFLDIWTYNAELLVLLENERTLDFHDSN

VKNLYEKVKSQLKNNAKEIGNGCFEFYHKCDNECMESVRNGTYDYP.

Avian M2 amino acid sequence -
                                           (SEQ ID NO: 10)
MSLLTEVETPTRNEWECRCSDSSDPIVVAANIIGILHLILWILDRLFFKC

IYRRLKYGLKRGPATAGVPESMREEYRQEQQSAVDVDDGHFVNIELE.

M2e (H1N1) amino acid sequence ->
                                           (SEQ ID NO: 11)
SLLTEVETPTRSEWECRCSDSSD.

M2e (H3N2) amino acid sequence -
                                           (SEQ ID NO: 12)
SLLTEVETPIRNEWGCRCNDSSD.

M2e (H5N1) amino acid sequence -
                                           (SEQ ID NO: 13)
SLLTEVETPTRNEWECRCSDSSD.

Anthrax EFn amino acid sequence -
                                           (SEQ ID NO: 14)
MNEHYTESDIKRNHKTEKNKTEKEKFKDSINNLVKTEFTNETLDKIQQTQ

DLLKKIPKDVLEIYSELGGEIYFTDIDLVEHKELQDLSEEEKNSMNSRGE

KVPFASRFVFEKKRETPKLIINIKDYAINSEQSKEVYYEIGKGISLDIIS

KDKSLDPEFLNLIKSLSDDSDSSDLLFSQKFKEKLELNNKSIDINFIKEN

LTEFQHAFSLAFSYYFAPDHRTVLELYAPDMFEYMNKLEKGGFEKISESL

KKEG.
```

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Roose, K., W. Fiers, and X. Saelens. 2009. Pandemic preparedness: toward a universal influenza vaccine. Drug news & perspectives 22: 80-92.

2. Pica, N., and P. Palese. 2013. Toward a universal influenza virus vaccine: prospects and challenges. Annual review of medicine 64: 189-202.

3. Wang, T. T., G. S. Tan, R. Hai, N. Pica, L. Ngai, D. C. Ekiert, I. A. Wilson, A. Garcia-Sastre, T. M. Moran, and P. Palese. 2010. Vaccination with a synthetic peptide from the influenza virus hemagglutinin provides protection against distinct viral subtypes. Proc Natl Acad Sci USA 107: 18979-18984.

4. Edwards, M. J., and N. J. Dimmock. 2000. Two influenza A virus-specific Fabs neutralize by inhibiting virus attachment to target cells, while neutralization by their IgGs is complex and occurs simultaneously through fusion inhibition and attachment inhibition. Virology 278: 423-435.

5. Gocnik, M., T. Fislova, V. Mucha, T. Sladkova, G. Russ, F. Kostolansky, and E. Vareckova. 2008. Antibodies induced by the HA2 glycopolypeptide of influenza virus hemagglutinin improve recovery from influenza A virus infection. J Gen Virol 89: 958-967.

6. Bommakanti, G., M. P. Citron, R. W. Hepler, C. Callahan, G. J. Heidecker, T. A. Najar, X. Lu, J. G. Joyce, J. W. Shiver, D. R. Casimiro, J. ter Meulen, X. Liang, and R. Varadarajan. 2010. Design of an HA2-based *Escherichia coli* expressed influenza immunogen that protects mice from pathogenic challenge. Proc Natl Acad Sci USA 107: 13701-13706.

7. Pinto, L. H., and R. A. Lamb. 2007. Controlling influenza virus replication by inhibiting its proton channel. Molecular bioSystems 3: 18-23.

8. Holsinger, L. J., and R. A. Lamb. 1991. Influenza virus M2 integral membrane protein is a homotetramer stabilized by formation of disulfide bonds. Virology 183: 32-43.

9. Kang, S. M., J. M. Song, and R. W. Compans. 2011. Novel vaccines against influenza viruses. Virus research 162: 31-38.

10. Kim, M. C., J. S. Lee, Y. M. Kwon, E. O, Y. J. Lee, J. G. Choi, B. Z. Wang, R. W. Compans, and S. M. Kang. 2013. Multiple heterologous M2 extracellular domains presented on virus-like particles confer broader and stronger M2 immunity than live influenza A virus infection. Antiviral research 99: 328-335.

11. Kim, M. C., J. M. Song, E. O, Y. M. Kwon, Y. J. Lee, R. W. Compans, and S. M. Kang. 2013. Virus-like particles containing multiple M2 extracellular domains confer improved cross-protection against various subtypes of influenza virus. Mol Ther 21: 485-492.

12. Wang, B. Z., H. S. Gill, S. M. Kang, L. Wang, Y. C. Wang, E. V. Vassilieva, and R. W. Compans. 2012. Enhanced influenza virus-like particle vaccines containing the extracellular domain of matrix protein 2 and a Toll-like receptor ligand. Clin Vaccine Immunol 19: 1119-1125.

13. Song, J. M., B. Z. Wang, K. M. Park, N. Van Rooijen, F. S. Quan, M. C. Kim, H. T. Jin, A. Pekosz, R. W. Compans, and S. M. Kang. 2011. Influenza virus-like particles containing M2 induce broadly cross protective immunity. PLoS One 6: e14538.

14. Kim, M. C., J. W. Lee, H. J. Choi, Y. N. Lee, H. S. Hwang, J. Lee, C. Kim, J. S. Lee, C. Montemagno, M. R. Prausnitz, and S. M. Kang. 2015. Microneedle patch delivery to the skin of virus-like particles containing heterologous M2e extracellular domains of influenza virus induces broad heterosubtypic cross-protection. J Control Release 210: 208-216.

15. Quesnel-Hellmann, A., A. Cleret, D. R. Vidal, and J. N. Tournier. 2006. Evidence for adjuvanticity of anthrax edema toxin. Vaccine 24: 699-702.

16. Duverger, A., J. M. Carre, J. Jee, S. H. Leppla, E. Cormet-Boyaka, W. J. Tang, D. Tome, and P. N. Boyaka. 2010. Contributions of edema factor and protective antigen to the induction of protective immunity by *Bacillus anthracis* edema toxin as an intranasal adjuvant. J Immunol 185: 5943-5952.

17. Kolla, R. V., S. Chintalapati, M. Sabet, E. Santelli, R. C. Liddington, M. David, J. Fierer, D. Guiney, and R. C. Rickert. 2007. Complement C3d conjugation to anthrax protective antigen promotes a rapid, sustained, and protective antibody response. PLoS One 2: e1044.

18. McEvers, K., M. Elrefaei, P. Norris, S. Deeks, J. Martin, Y. Lu, and H. Cao. 2005. Modified anthrax fusion proteins deliver HIV antigens through WIC Class I and II pathways. Vaccine 23: 4128-4135.

19. Shaw, C. A., and M. N. Starnbach. 2008. Both CD4+ and CD8+ T cells respond to antigens fused to anthrax lethal toxin. Infect Immun 76: 2603-2611.

20. Zeng, M., Q. Xu, E. D. Hesek, and M. E. Pichichero. 2006. N-fragment of edema factor as a candidate antigen for immunization against anthrax. Vaccine 24: 662-670.

21. Zeng, M., Q. Xu, and M. E. Pichichero. 2007. Protection against anthrax by needle-free mucosal immunization with human anthrax vaccine. Vaccine 25: 3588-3594.

22. Xu, Q., E. D. Hesek, and M. Zeng. 2007. Transcriptional stimulation of anthrax toxin receptors by anthrax edema toxin and *Bacillus anthracis* Sterne spore. Microb Pathog 43: 37-45. PMID: 17459655.

23. Xu, Q., and M. Zeng. 2008. Detoxified lethal toxin as a potential mucosal vaccine against anthrax. Clin Vaccine Immunol 15: 612-616.

24. EBS. BioThrax (R) Anthrax Vaccine Adsorbed Dosage and Administration.

25. Twentyman, P. R., and M. Luscombe. 1987. A study of some variables in a tetrazolium dye (MTT) based assay for cell growth and chemosensitivity. Br J Cancer 56: 279-285.

26. Hashemi, H., S. Pouyanfard, M. Bandehpour, Z. Noroozbabaei, B. Kazemi, X. Saelens, and T. Mokhtari-Azad. 2012. Immunization with M2e-displaying T7 bacteriophage nanoparticles protects against influenza A virus challenge. PLoS One 7: e45765.

27. Bui, H. H., B. Peters, E. Assarsson, I. Mbawuike, and A. Sette. 2007. Ab and T cell epitopes of influenza A virus, knowledge and opportunities. Proc Natl Acad Sci USA 104: 246-251.

28. Hori, S., T. Nomura, and S. Sakaguchi. 2003. Control of regulatory T cell development by the transcription factor Foxp3. Science 299: 1057-1061.

29. WHO. 2009. Influenza (Seasonal) Fact sheet.

30. Reperant, L. A., G. F. Rimmelzwaan, and T. Kuiken. 2009. Avian influenza viruses in mammals. Revue scientifique et technique (International Office of Epizootics) 28: 137-159.

31. Li, J., M. T. Arevalo, Y. Chen, O. Posadas, J. A. Smith, and M. Zeng. 2014. Intranasal immunization with influenza antigens conjugated with cholera toxin subunit B stimulates broad spectrum immunity against influenza viruses. Human vaccines & immunotherapeutics 10.

32. Dreyfus, C., N. S. Laursen, T. Kwaks, D. Zuijdgeest, R. Khayat, D. C. Ekiert, J. H. Lee, Z. Metlagel, M. V. Bujny, M. Jongeneelen, R. van der Vlugt, M. Lamrani, H. J. Korse, E. Geelen, O. Sahin, M. Sieuwerts, J. P. Brakenhoff, R. Vogels, O. T. Li, L. L. Poon, M. Peiris, W. Koudstaal, A. B. Ward, I. A. Wilson, J. Goudsmit, and R. H. Friesen. 2012. Highly conserved protective epitopes on influenza B viruses. Science (New York, N.Y.) 337: 1343-1348.

33. Denkers, E. Y., C. C. Badger, J. A. Ledbetter, and I. D. Bernstein. 1985. Influence of antibody isotype on passive serotherapy of lymphoma. J Immunol 135: 2183-2186.

34. Jegerlehner, A., N. Schmitz, T. Storni, and M. F. Bachmann. 2004. Influenza A vaccine based on the extracellular domain of M2: weak protection mediated via antibody-dependent NK cell activity. Journal of immunology 172: 5598-5605.

35. Kim, M. C., Y. N. Lee, E. J. Ko, J. S. Lee, Y. M. Kwon, H. S. Hwang, J. M. Song, B. M. Song, Y. J. Lee, J. G. Choi, H. M. Kang, F. S. Quan, R. W. Compans, and S. M. Kang. 2014. Supplementation of influenza split vaccines with conserved M2 ectodomains overcomes strain specificity and provides long-term cross protection. Molecular therapy: the journal of the American Society of Gene Therapy 22: 1364-1374.

36. Betts, R. J., N. Prabhu, A. W. Ho, F. C. Lew, P. E. Hutchinson, O. Rotzschke, P. A. Macary, and D. M. Kemeny. 2012. Influenza A virus infection results in a robust, antigen-responsive, and widely disseminated Foxp3+ regulatory T cell response. J Virol 86: 2817-2825.

37. Brincks, E. L., A. D. Roberts, T. Cookenham, S. Sell, J. E. Kohlmeier, M. A. Blackman, and D. L. Woodland. 2013. Antigen-specific memory regulatory CD4+Foxp3+ T cells control memory responses to influenza virus infection. J Immunol 190: 3438-3446.

38. Bedoya, F., G. S. Cheng, A. Leibow, N. Zakhary, K. Weissler, V. Garcia, M. Aitken, E. Kropf, D. S. Garlick, E.

J. Wherry, J. Erikson, and A. J. Caton. 2013. Viral antigen induces differentiation of Foxp3+ natural regulatory T cells in influenza virus-infected mice. J Immunol 190: 6115-6125.

39. Moise, L., F. Terry, A. H. Gutierrez, R. Tassone, P. Losikoff, S. H. Gregory, C. Bailey-Kellogg, W. D. Martin, and A. S. De Groot. 2014. Smarter vaccine design will circumvent regulatory T cell-mediated evasion in chronic HIV and HCV infection. Frontiers in microbiology 5: 502.

40. Comer, J. E., A. K. Chopra, J. W. Peterson, and R. Konig. 2005. Direct inhibition of T-lymphocyte activation by anthrax toxins in vivo. Infect Immun 73: 8275-8281.

41. Barbey-Martin, C., B. Gigant, T. Bizebard, L. J. Calder, S. A. Wharton, J. J. Skehel, and M. Knossow. 2002. An antibody that prevents the hemagglutinin low pH fusogenic transition. Virology 294: 70-74.

What is claimed is:

1. An antigenic fusion protein comprising: three or more different influenza A ectodomains of matrix protein 2 (M2e) domains; one or more stem regions from a first influenza A hemagglutinin 2(HA2) protein domains; and an anthrax antigen, wherein the fusion protein is immunogenic across influenza strains.

2. The fusion protein of claim 1, wherein the fusion protein further comprises, or is provided with, an adjuvant selected from at least one of cholera toxin B subunit, flagellin, human papillomavirus L1 or L2 protein, herpes simplex glycoprotein D (gD), complement C4binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles.

3. The fusion protein of claim 1, wherein influenza A ectodomains are selected from H1N1, H3N2, or H5N1.

4. The fusion protein of claim 1, further comprises a stem region from a second influenza A hemagglutinin 2 (HA2) protein domain which is from a different strain than the first HA2 protein domain.

5. The fusion protein of claim 1, further comprising one or more immunogenic adjuvants.

6. The fusion protein of claim 1, further comprising one or more pharmaceutically acceptable excipients for intraperitoneal, subcutaneous, intranasal, intramuscular, oral, topical or transdermal administration.

7. The fusion protein of claim 1, wherein the antigen further comprises at least one of a pharmaceutically acceptable diluent, excipient, carrier, solubilizing agent, emulsifying agent, or preservative.

8. The fusion protein of claim 1, wherein the antigen comprises 4, 5, 6, 7, 8, 9, or 10 ectodomains of influenza A Matrix Protein 2 (M2e).

9. The fusion protein of claim 1, wherein the antigen comprises 2, 3, 4, 5, 6, 7, 8, 9, or 10 stem region of an influenza A hemagglutinin 2 (HA2) protein.

10. The fusion protein of claim 1, wherein the three or more ectodomains of influenza A Matrix Protein 2 (M2e) are separated by peptide linkers comprising one to 20 amino acids.

11. The fusion protein of claim 1, wherein the antigen is a fusion protein that comprises amino acids encoded by nucleic acids having SEQ ID NOS.: 1, 2, 3, 4, 5 and 6.

12. The fusion protein of claim 1, wherein the antigen is a fusion protein that comprises, in the following order, amino acids encoded by nucleic acids having SEQ ID NOS.: 1, 2, 3, 4, 5 and 6.

13. The fusion protein of claim 1, wherein the antigen is a fusion protein that comprises amino acids encoded by nucleic acids having SEQ ID NOS.: 1, 2, 3, 4, 5 and 6 separated by one or more linkers.

14. The fusion protein of claim 1, wherein the linkers have the sequences Ala-Ala-Ala or Gly-Ser.

15. The fusion protein of claim 1, wherein the antigen is a fusion protein that comprises three or more amino acids peptides of SEQ ID NOS.: 11, 12, and 13, at least one peptide of amino acid sequence SEQ ID NOS.: 9 or 10, and a peptide of SEQ ID NO.: 14.

16. The fusion protein of claim 1, wherein the fusion protein is, in order, SEQ ID NO.: 14, SEQ ID NOS.: 11, 12, and 13 in any order, and SEQ ID NOS.: 9 or 10.

17. The fusion protein of claim 1, wherein the fusion protein is, in order, SEQ ID NOS.: 11, 12, and 13 in any order, and SEQ ID NOS.: 9 or 10.

18. A nucleic acid encoding the fusion protein of claim 1.

19. A method of making a mucosal vaccine against influenza A comprising:
combining two or more different influenza A ectodomains of Matrix Protein 2 (M2e); one or more stem regions from a first influenza A hemagglutinin 2 (HA2) protein; and an anthrax antigen into an antigen that is immunogenic across strains.

20. The method of claim 19, wherein the vaccine further comprises, or is provided with, an adjuvant selected from at least one of anthrax protective antigen (PA), cholera toxin B subunit, flagellin, human papillomavirus L1 or L2 protein, herpes simplex glycoprotein D (gD), complement C4 binding protein, TL4 ligand, and 1L-1 beta, aluminum salt, Freund's complete or incomplete adjuvant, lysolecithin, pluronic polyols, polyanions, an oil-water emulsion, dinitrophenol, iscomatrix, and liposome polycation DNA particles.

21. The method of claim 19, wherein the two or more different influenza ectodomains are selected from H1N1, H3N2, or H5N1.

22. The method of claim 19, further comprising a second stem region of an influenza A hemagglutinin 2 (HA2) protein from a different influenza virus A strain than the first HA2 protein.

23. The method of claim 19, further comprising one or more immunogenic adjuvants.

24. The method of claim 19, further comprising one or more pharmaceutically acceptable excipients for intraperitoneal, subcutaneous, intranasal, intramuscular, oral, topical or transdermal administration.

25. The method of claim 19, wherein the antigen further comprises at least one of a pharmaceutically acceptable diluent, excipient, carrier, solubilizing agent, emulsifying agent, or preservative.

26. The method of claim 19, wherein the antigen comprises 3, 4, 5, 6, 7, 8, 9 or 10 ectodomains of influenza A Matrix Protein 2 (M2e).

27. The method of claim 19, wherein the antigen comprises 3, 4, 5, 6, 7, 8, 9 or 10 stem region of an influenza A hemagglutinin 2 (HA2) protein.

28. The method of claim 19, wherein the antigen comprises 3 ectodomains of influenza A Matrix Protein 2 (M2e) separated by peptide linkers comprising one to 20 amino acids.

29. The method of claim 19, wherein the antigen is a fusion protein that comprises SEQ ID NOS.: 1, 2, 3, 4, 5 and 6.

30. The method of claim 19, wherein the antigen is a fusion protein that comprises, in the following order, SEQ ID NOS.: 1, 2, 3, 4, 5 and 6.

31. The method of claim 19, wherein the antigen is a fusion protein that comprises SEQ ID NOS.: 1, 2, 3, 4, 5 and 6 separated by one or more amino acid or peptide linkers.

32. The method of claim 19, wherein the linkers have the sequences Ala-Ala-Ala or Gly-Ser.

33. The method of claim 19, wherein the antigen is a fusion protein that comprises three or more amino acids peptides of SEQ ID NOS.: 11, 12, and 13, at least one peptide of amino acid sequence SEQ ID NOS.: 9 or 10, and a peptide of SEQ ID NO.: 14.

34. The method of claim 19, wherein the fusion protein is, in order, SEQ ID NO.: 14, SEQ ID NOS.: 11, 12, and 13 in any order, and SEQ ID NOS.: 9 or 10.

35. The method of claim 19, wherein the fusion protein is, in order, SEQ ID NOS.: 11, 12, and 13 in any order, and SEQ ID NOS.: 9 or 10.

36. A method of evaluating a candidate drug believed to provide cross-immunity against Influenza A and anthrax, the method comprising:
(a) measuring the immune response from a set of patients suspected of having or being exposed to influenza A;
(b) administering a candidate drug to a first subset of the patients, and a placebo to a second subset of the patients, wherein the candidate drug comprises: two or more different influenza A ectodomains of Matrix Protein 2 (M2e); one or more stem regions of an influenza A hemagglutinin 2 (HA2) protein; and an anthrax antigen into a fusion protein that is immunogenic across strains;
(c) repeating step (a) after the administration of the candidate drug or the placebo; and
(d) determining if the candidate drug triggers an increase in the immune response against two or more influenza A strains and anthrax that is statistically significant as compared to any increase occurring in the second subset of patients, wherein a statistically significant increase indicates that the candidate drug is useful in treating two or more strains of influenza A and anthrax.

37. An isolated immune response stimulating fusion protein against influenza A comprising:
two or more different influenza ectodomains of A Matrix Protein 2 (M2e); one or more stem regions of an influenza A hemagglutinin 2 (HA2) protein comprising SEQ ID NO.: 14, SEQ ID NOS.: 11, 12, and 13 in any order, and SEQ ID NOS.: 9 or 10 into a fusion protein that is immunogenic across strains.

* * * * *

SEQUENCE LISTING

```
<160> NUMBER OF SEQ ID NOS: 14

<210> SEQ ID NO 1
<211> LENGTH: 480
<212> TYPE: DNA
<213> ORGANISM: Artificial Sequence
<220> FEATURE:
<223> OTHER INFORMATION: Synthetic primer

<400> SEQUENCE: 1
ggtctatttg gagccattgc cggttttatt gaaggggat ggactggaat gatagatgga      60
tggtatggtt atcatcatca gaatgaacag ggatcaggct atgcagcgga tcaaaaaagc    120
acacaaaatg ccattgacgg gattacaaac aaggtgaact ctgttatcga gaaatgaac    180 actcaattca cagctgtggg taaagaattc aacaaattag aaaaaaggat tgaaaattta    240
aataaaaaag ttgatgatgg atttctggac atttggacat ataatgcaga attgttagtt    300
ctactggaaa atgaaaggac tctggatttc catgactcaa atgtgaagaa tctgtatgag    360
aaagtaaaaa gccaattaaa gaataatgcc aaagaaatcg gaatggatg ttttgagttc    420 taccacaagt gtgacaatga atgcatggaa agtgtaagaa atgggactta tgattatccc    480

<210> SEQ ID NO 2
<211> LENGTH: 294
<212> TYPE: DNA
<213> ORGANISM: Artificial Sequence
<220> FEATURE:
<223> OTHER INFORMATION: Synthetic primer

<400> SEQUENCE: 2
atgtctctgc tgaccgaagt tgaaaccccg acccgtaacg aatgggaatg ccgttgctct     60
gactcttctg acccgatcgt tgttgcggcg aacatcatcg gtatcctgca cctgatcctg    120
tggatcctgg accgtctgtt cttcaaatgc atctaccgtc gtctgaagta cggtctgaaa    180
cgtggtccgg cgaccgcggg tgttccagaa tctatgcgtg aagaataccg tcaggaacag    240
cagtctgcgg ttgacgttga tgacggtcac ttcgttaaca tcgaactgga ataa          294

<210> SEQ ID NO 3
<211> LENGTH: 69
<212> TYPE: DNA
<213> ORGANISM: Artificial Sequence
<220> FEATURE:
<223> OTHER INFORMATION: Synthetic primer

<400> SEQUENCE: 3
agtcttctaa ccgaggtcga aacgcctacc agaagcgaat gggagtgcag atgcagcgat     60
tcaagtgat                                                             69

<210> SEQ ID NO 4
<211> LENGTH: 69
<212> TYPE: DNA
<213> ORGANISM: Artificial Sequence
<220> FEATURE:
```

<223> OTHER INFORMATION: Synthetic primer

<400> SEQUENCE: 4

```
agccttctaa ccgaggtcga aacgcctatc agaaacgaat gggggtgcag atgcaacgat      60
tcaagtgac                                                              69
```

<210> SEQ ID NO 5
<211> LENGTH: 69
<212> TYPE: DNA
<213> ORGANISM: Artificial Sequence
<220> FEATURE:
<223> OTHER INFORMATION: Synthetic primer

<400> SEQUENCE: 5

```
agtcttctaa ccgaggtcga aacgcctacc agaaacgaat gggagtgcag atgcagcgat      60
tcaagtgat                                                              69
```

<210> SEQ ID NO 6
<211> LENGTH: 765
<212> TYPE: DNA
<213> ORGANISM: Artificial Sequence
<220> FEATURE:
<223> OTHER INFORMATION: Synthetic primer

<400> SEQUENCE: 6

```
atgaatgaac attacactga gagtgatatt aaaagaaacc ataaaactga aaaaataaa       60
actgaaaaag aaaaatttaa agacagtatt aataacttag ttaaaacaga atttaccaat     120
gaaactttag ataaaataca gcagacacaa gacttattaa aaaagatacc taaggatgta     180
cttgaaattt atagtgaatt aggaggagaa atctatttta cagatataga tttagtagaa     240
cataaggagt tacaagattt aagtgaagaa gagaaaaata gtatgaatag tagaggtgaa     300
aaagttccgt ttgcatcccg ttttgtattt gaaaagaaaa gggaaacacc taaattaatt     360
ataaatatca aagattatgc aattaatagt gaacaaagta agaagtata ttatgaaatt       420
ggaaagggga tttctcttga tattataagt aaggataaat ctctagatcc agagttttta     480
aatttaatta gagtttaag tgatgatagt gatagtagcg acctttttatt tagtcaaaaa     540
tttaaagaga agctagaatt gaataataaa agtatagata taaattttat aaaagaaaat     600
ttaactgaat tcagcatgc gttttcttta gcgttttctt attatttgc acctgaccat        660
agaacggtat tagagttata tgcccccgac atgtttgagt atatgaataa gttagaaaaa     720
gggggatttg agaaaataag tgaaagtttg aagaagaag gttaa                      765
```

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

```
Ser Leu Leu Thr Glu Val Glu Thr Pro Ile Arg Asn Glu Trp Gly Ser
1               5                   10                  15
```

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Val Glu Thr Pro Ile Arg Asn Glu Trp
1               5

<210> SEQ ID NO 9
<211> LENGTH: 146
<212> TYPE: PRT
<213> ORGANISM: Artificial Sequence
<220> FEATURE:
<223> OTHER INFORMATION: Synthetic peptide

<400> SEQUENCE: 9

Gly Leu Phe Gly Ala Ile Ala Gly Gly Tyr His His Gln Asn Glu Gln
1               5                   10                  15

Gly Ser Gly Tyr Ala Ala Asp Gln Lys Ser Thr Gln Asn Ala Ile Asp
            20                  25                  30

Gly Ile Thr Asn Lys Val Asn Ser Val Ile Glu Lys Met Asn Thr Gln
        35                  40                  45

Phe Thr Ala Val Gly Lys Glu Phe Asn Lys Leu Glu Lys Arg Ile Glu
    50                  55                  60

Asn Leu Asn Lys Lys Val Asp Asp Gly Phe Leu Asp Ile Trp Thr Tyr
65                  70                  75                  80

Asn Ala Glu Leu Leu Val Leu Leu Glu Asn Glu Arg Thr Leu Asp Phe
                85                  90                  95

His Asp Ser Asn Val Lys Asn Leu Tyr Glu Lys Val Lys Ser Gln Leu
            100                 105                 110

Lys Asn Asn Ala Lys Glu Ile Gly Asn Gly Cys Phe Glu Phe Tyr His
        115                 120                 125

Lys Cys Asp Asn Glu Cys Met Glu Ser Val Arg Asn Gly Thr Tyr Asp
    130                 135                 140

Tyr Pro
145

<210> SEQ ID NO 10
<211> LENGTH: 97
<212> TYPE: PRT
<213> ORGANISM: Artificial Sequence
<220> FEATURE:
<223> OTHER INFORMATION: Synthetic peptide

<400> SEQUENCE: 10

Met Ser Leu Leu Thr Glu Val Glu Thr Pro Thr Arg Asn Glu Trp Glu
1               5                   10                  15

Cys Arg Cys Ser Asp Ser Ser Asp Pro Ile Val Val Ala Ala Asn Ile
            20                  25                  30

Ile Gly Ile Leu His Leu Ile Leu Trp Ile Leu Asp Arg Leu Phe Phe
        35                  40                  45

Lys Cys Ile Tyr Arg Arg Leu Lys Tyr Gly Leu Lys Arg Gly Pro Ala
    50                  55                  60

Thr Ala Gly Val Pro Glu Ser Met Arg Glu Glu Tyr Arg Gln Glu Gln
65                  70                  75                  80

Gln Ser Ala Val Asp Val Asp Asp Gly His Phe Val Asn Ile Glu Leu
                85                  90                  95

Glu

<210> SEQ ID NO 11
<211> LENGTH: 23
<212> TYPE: PRT

```
<213> ORGANISM: Artificial Sequence
<220> FEATURE:
<223> OTHER INFORMATION: Synthetic peptide

<400> SEQUENCE: 11

Ser Leu Leu Thr Glu Val Glu Thr Pro Thr Arg Ser Glu Trp Glu Cys
1               5                   10                  15

Arg Cys Ser Asp Ser Ser Asp
            20

<210> SEQ ID NO 12
<211> LENGTH: 23
<212> TYPE: PRT
<213> ORGANISM: Artificial Sequence
<220> FEATURE:
<223> OTHER INFORMATION: Synthetic peptide

<400> SEQUENCE: 12

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic peptide

<400> SEQUENCE: 13

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 14
<211> LENGTH: 254
<212> TYPE: PRT
<213> ORGANISM: Artificial Sequence
<220> FEATURE:
<223> OTHER INFORMATION: Synthetic peptide

<400> SEQUENCE: 14

Met Asn Glu His Tyr Thr Glu Ser Asp Ile Lys Arg Asn His Lys Thr
1               5                   10                  15

Glu Lys Asn Lys Thr Glu Lys Glu Lys Phe Lys Asp Ser Ile Asn Asn
                20                  25                  30

Leu Val Lys Thr Glu Phe Thr Asn Glu Thr Leu Asp Lys Ile Gln Gln
            35                  40                  45

Thr Gln Asp Leu Leu Lys Lys Ile Pro Lys Asp Val Leu Glu Ile Tyr
        50                  55                  60

Ser Glu Leu Gly Gly Glu Ile Tyr Phe Thr Asp Ile Asp Leu Val Glu
65                  70                  75                  80

His Lys Glu Leu Gln Asp Leu Ser Glu Glu Lys Asn Ser Met Asn
                85                  90                  95

Ser Arg Gly Glu Lys Val Pro Phe Ala Ser Arg Phe Val Phe Glu Lys
                100                 105                 110

Lys Arg Glu Thr Pro Lys Leu Ile Ile Asn Ile Lys Asp Tyr Ala Ile
            115                 120                 125

Asn Ser Glu Gln Ser Lys Glu Val Tyr Tyr Glu Ile Gly Lys Gly Ile
```

-continued

```
            130                 135                 140
Ser Leu Asp Ile Ile Ser Lys Asp Lys Ser Leu Asp Pro Glu Phe Leu
145                 150                 155                 160

Asn Leu Ile Lys Ser Leu Ser Asp Asp Ser Asp Ser Ser Asp Leu Leu
                165                 170                 175

Phe Ser Gln Lys Phe Lys Glu Lys Leu Glu Leu Asn Asn Lys Ser Ile
                180                 185                 190

Asp Ile Asn Phe Ile Lys Glu Asn Leu Thr Glu Phe Gln His Ala Phe
                195                 200                 205

Ser Leu Ala Phe Ser Tyr Tyr Phe Ala Pro Asp His Arg Thr Val Leu
                210                 215                 220

Glu Leu Tyr Ala Pro Asp Met Phe Glu Tyr Met Asn Lys Leu Glu Lys
225                 230                 235                 240

Gly Gly Phe Glu Lys Ile Ser Glu Ser Leu Lys Lys Glu Gly
                245                 250
```